(12) United States Patent
Bommarito et al.

(10) Patent No.: US 11,260,140 B2
(45) Date of Patent: Mar. 1, 2022

(54) MICROBIAL INDICATOR DEVICE FOR USE WITH PROCESS MONITORING SYSTEMS

(71) Applicant: 3M INNOVATIVE PROPERTIES COMPANY, Saint Paul, MN (US)

(72) Inventors: G. Marco Bommarito, Stillwater, MN (US); Timothy J. Nies, Stillwater, MN (US); Barry W. Robole, Woodville, WI (US); Assumpta A. G. Bennaars-Eiden, Woodbury, MN (US); Jodi L. Connell, Saint Paul, MN (US); Tonya D. Bonilla, Woodbury, MN (US); Timothy A. Kohman, Cottage Grove, MN (US); Ruthann R. Duda, Eagan, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 291 days.

(21) Appl. No.: 16/341,209

(22) PCT Filed: Oct. 12, 2017

(86) PCT No.: PCT/US2017/056250
§ 371 (c)(1),
(2) Date: Apr. 11, 2019

(87) PCT Pub. No.: WO2018/071618
PCT Pub. Date: Apr. 19, 2018

(65) Prior Publication Data
US 2019/0255208 A1 Aug. 22, 2019

Related U.S. Application Data

(60) Provisional application No. 62/407,749, filed on Oct. 13, 2016.

(51) Int. Cl.
*A61L 2/28* (2006.01)
*C12Q 1/22* (2006.01)

(52) U.S. Cl.
CPC .................. *A61L 2/28* (2013.01); *C12Q 1/22* (2013.01); *A61L 2202/24* (2013.01)

(58) Field of Classification Search
CPC .......... A61L 2/28; A61L 2202/24; C12Q 1/22
See application file for complete search history.

(56) References Cited

U.S. PATENT DOCUMENTS 4,539,256 A 9/1985 Shipman
4,726,989 A 2/1988 Mrozinski
(Continued)

FOREIGN PATENT DOCUMENTS

WO WO 2010-045138 4/2010
WO WO 2010-071764 6/2010
(Continued)

OTHER PUBLICATIONS

Colowick, Methods in Enzymology, (174-212), 1957.
(Continued)

*Primary Examiner* — Regina M Yoo

(57) ABSTRACT

A microbial indicator device for liquid disinfection comprises a first cavity, a source of biological activity fluidically coupled to the first cavity via a portion of a first fluidic path, a filter membrane positioned in a second fluidic path for a disinfectant, and a first coupling portion fluidically coupled to the source of biologically activity via the second fluidic path. The filter membrane has a first side and a second side, wherein the first side is in fluid communication with the first fluidic path. The filter membrane has a pore size sufficient to retain at least a portion of the source of biological activity on the first side. The device further comprises a frangible container contained in the first cavity, wherein a liquid in the (Continued)

container is in fluid communication with the first cavity when the container is fractured.

18 Claims, 18 Drawing Sheets

(56) References Cited

U.S. PATENT DOCUMENTS

| | | | |
|---|---|---|---|
| 4,867,881 A | | 9/1989 | Kinzer |
| 5,120,594 A | | 6/1992 | Mrozinski |
| 5,260,360 A | | 11/1993 | Mrozinski |
| 5,302,299 A | * | 4/1994 | Pascale ............... A61M 1/3643 210/767 |
| 5,750,184 A | | 5/1998 | Imburgia |

FOREIGN PATENT DOCUMENTS

| | | |
|---|---|---|
| WO | WO 2010-078234 | 7/2010 |
| WO | WO 2011-152967 | 12/2011 |
| WO | WO 2011-153085 | 12/2011 |
| WO | WO 2013-122852 | 8/2013 |
| WO | WO 2016-164329 | 10/2016 |
| WO | WO 2017-184444 | 10/2017 |
| WO | WO 2017-192305 | 11/2017 |
| WO | WO 2017-192306 | 11/2017 |
| WO | WO 2018-125798 | 7/2018 |

OTHER PUBLICATIONS

Glick, Methods of Biochemical Analysis, (189-192), 1969.
Udenfriend, Fluorescence Assay in Biology and Medicine, (312-348), 1962.
International Search Report for PCT International Application No. PCT/US2017/056250, dated Mar. 23, 2018, 4 pages.

* cited by examiner

MICROBIAL INDICATOR DEVICE FOR USE WITH PROCESS MONITORING SYSTEMS

CROSS REFERENCE TO RELATED APPLICATIONS

This application is a national stage filing under 35 U.S.C. 371 of PCT/US2017/056250, filed Oct. 12, 2017, which claims the benefit of U.S. Provisional Application No. 62/407,749, filed Oct. 13, 2016, the disclosures of which are incorporated by reference in their entirety herein.

BACKGROUND

The present disclosure generally relates to microbial indicator devices for use with process monitoring systems, and particularly, for use with process monitoring systems configured to monitor endoscope reprocessing systems.

Endoscopy procedures play a beneficial role in the prevention, diagnosis and treatment of disease. Endoscopy procedures are performed using complex, reusable, flexible instruments that, when inserted into the body, may become heavily contaminated with patient biomaterial and microorganisms, including potential pathogens. Careful reprocessing of flexible endoscopes between patients is critical to reducing the risk of cross-contamination and the possible transmission of pathogens.

The U.S. Food and Drug Administration (FDA) distinguishes cleaning, disinfection, and sterilization. Cleaning is the physical removal of organic material or soil from objects, usually done by using water with or without detergents. Generally, cleaning is designed to remove rather than to kill microorganisms. Disinfection is the destruction of pathogenic and other kinds of microorganisms by thermal or chemical means. Disinfection is a generally a less lethal process than sterilization, because it destroys most recognized pathogenic microorganisms, but not necessarily all microbial forms, such as bacterial spores. Sterilization is a validated process used to render product free from viable microorganisms.

Flexible endoscopes are rated as semi-critical according to the Spaulding classification for medical devices and therefore it is required that these devices be decontaminated by high-level disinfection. Thus, it is recommended that both endoscopes and reusable accessories be frequently visually inspected in the course of their use and reprocessing, including before, during and after use, as well as after cleaning and before high-level disinfection. However, a visually based method of verification has severe limitations when applied to flexible endoscopes because the complex, narrow lumens in these devices cannot be directly visually inspected.

Automated endoscope reprocessors (AERs) are used to clean and disinfect flexible endoscopes to a level that mitigates transmission of pathogenic organisms and disease between patients who are subject to an endoscopic procedure. Typically, the only information available to a user is the parametric information provided by the AER equipment itself which consists primarily of time and temperature information. The AER does not monitor chemical parameters capable of establishing the effectiveness of the disinfection cycle.

A microbial indicator device that incorporates a biological indicator (e.g., a carrier that has a source of biological activity disposed thereon) can provide feedback on the effectiveness of the disinfection cycle. In some solutions, a biological indicator is placed within a disinfectant flowpath of an AER which can cause a portion of the source of biological activity (e.g., vegetative organisms) to become dislodged in the disinfectant fluidic path contaminate the AER.

SUMMARY

Aspects of the present disclosure provide for a microbial indicator device that includes a filter membrane to be placed within a fluidic path after a disinfectant contacts a source of biological activity.

The microbial indicator device can include a first housing. The first housing can have a first cavity. The first housing can include a source of biologicial activity that is fluidically coupled to the first cavity via a portion of a first fluidic path. The first housing can also have a first coupling portion. The first coupling portion can have a first channel extending longitudinally therethrough that defines a portion of a second fluidic path. The first coupling portion is fluidically coupled the source of biologically activity via the second fluidic path.

The microbial indicator device can include a filter membrane positioned in the second fluidic path. The filter membrane has a first side and a second side and the first side is in fluid communication with the first fluidic path. The filter membrane has a pore size sufficient to retain at least a portion of the source of biological activity on the first side. The second side of the filter membrane defines the second side of the filter membrane.

DETAILED DESCRIPTION

Figure 1:
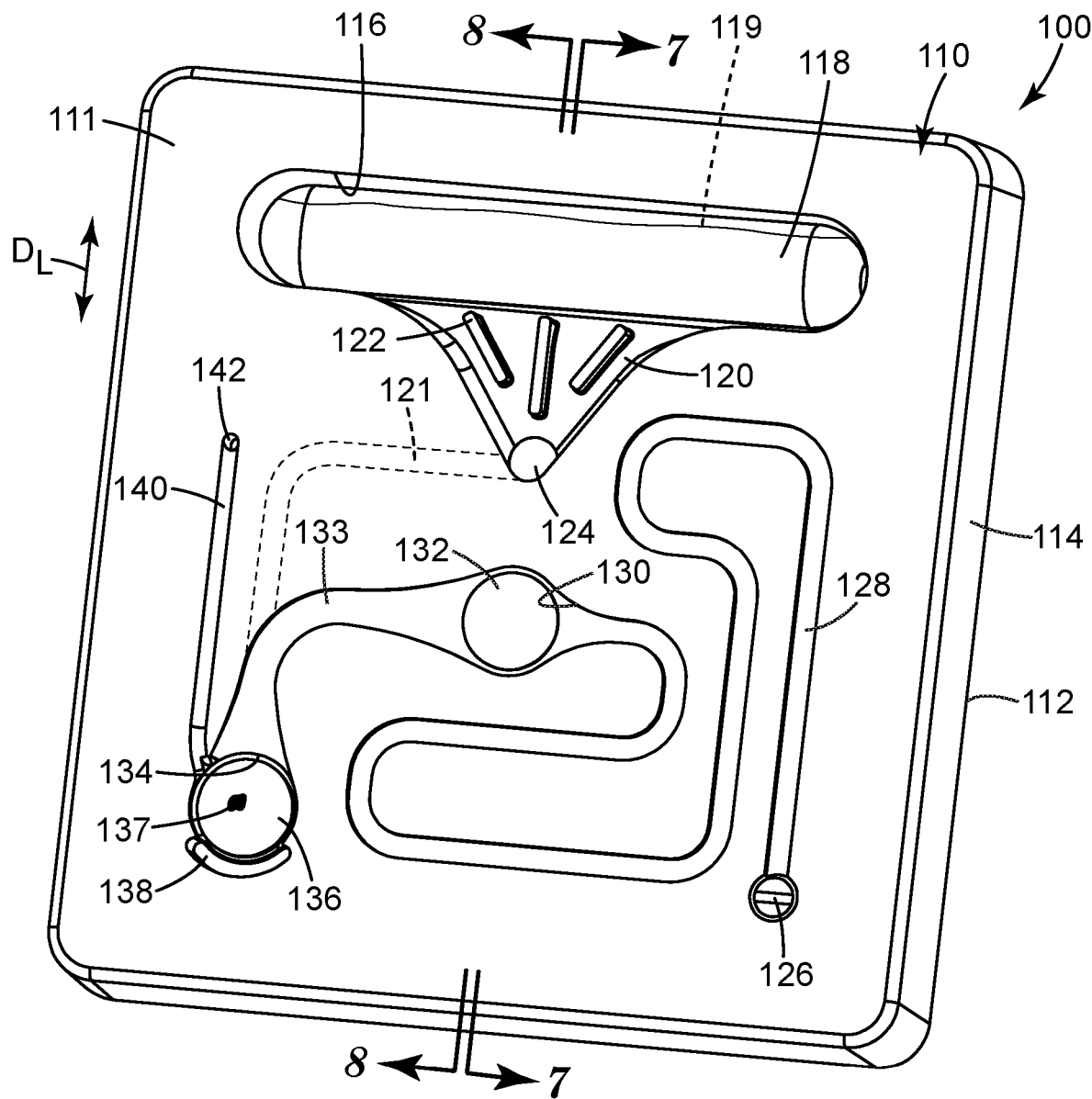
FIG. 1 is a front perspective view of a microbial indicator device according to one embodiment of the present disclosure.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "supported," and "coupled" and variations thereof are used broadly and encompass both direct and indirect supports, and couplings. Further, "connected" and "coupled" are not restricted to physical or mechanical connections or couplings. It is to be understood that other embodiments may be utilized, and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

Aspects of the present disclosure relate to a microbial indicator device that provides filtering of a source of biological activity for a fluidic path. The filtering can result in a pressure differential of no greater than 10% of an input pressure.

The microbial indicator device can be used with a process monitoring system. The process monitoring system can be used to monitor the effectiveness of a variety of reprocessing systems, including various cleaning, disinfecting, and/or liquid sterilization processes or systems. For example, in some embodiments, process monitoring systems of the present disclosure can be used to monitor an endoscope reprocessing system. Such an endoscope reprocessing system can include, but is not limited to, an automated endoscope reprocessor (AER), an endoscope cleaning reprocessor (ECR), a liquid chemical sterilization (LCS) system, or the like, or a combination thereof. By way of example only, the process monitoring systems of the present disclosure can be particularly useful for monitoring the effectiveness of a disinfection cycle provided by an AER. As a result, the cartridges, adapters, and systems of the present disclosure are sometimes described herein with reference to use with an AER. However, it should be understood that the cartridges, adapters, and systems of the present disclosure can be used in monitoring other endoscope reprocessing systems, as well as other cleaning, disinfecting, and/or liquid sterilization processes or systems. For example, although references are made to disinfection processes throughout this disclosure, aspects of the present disclosure relate to liquid sterilization processes as well.

The microbial indicator device can be a cartridge which can be stand-alone or used with an adaptor but nothing in this disclosure should limit the microbial indicator device to only a cartridge or to only a cartridge that can only be used with an adaptor. Cartridges of the present disclosure can be a consumable component of the system and can be configured to be removably received in a receptacle of an adapter (shown in FIG. 10). Adapters of the present disclosure can provide a means for effectively connecting (i.e., for fluid communication) the cartridge to a reprocessing system that is to be monitored for its effectiveness. In some embodiments, the adaptor can be referred to as a manifold.

The microbial indicator device can have an internal tortuous path designed to mimic the resistance to flow of a medical device. Thus, in some embodiments, the microbial indicator device can function as a process challenge device.

The microbial indicator device of the present disclosure can include various features of a cartridge described in U.S. Application No. 62/326,329, filed Apr. 22, 2016 and a microbial indicator device described in U.S. Application No. 62/145,323, filed Apr. 9, 2015, which are incorporated herein by reference in their entirety.

Figure 10:
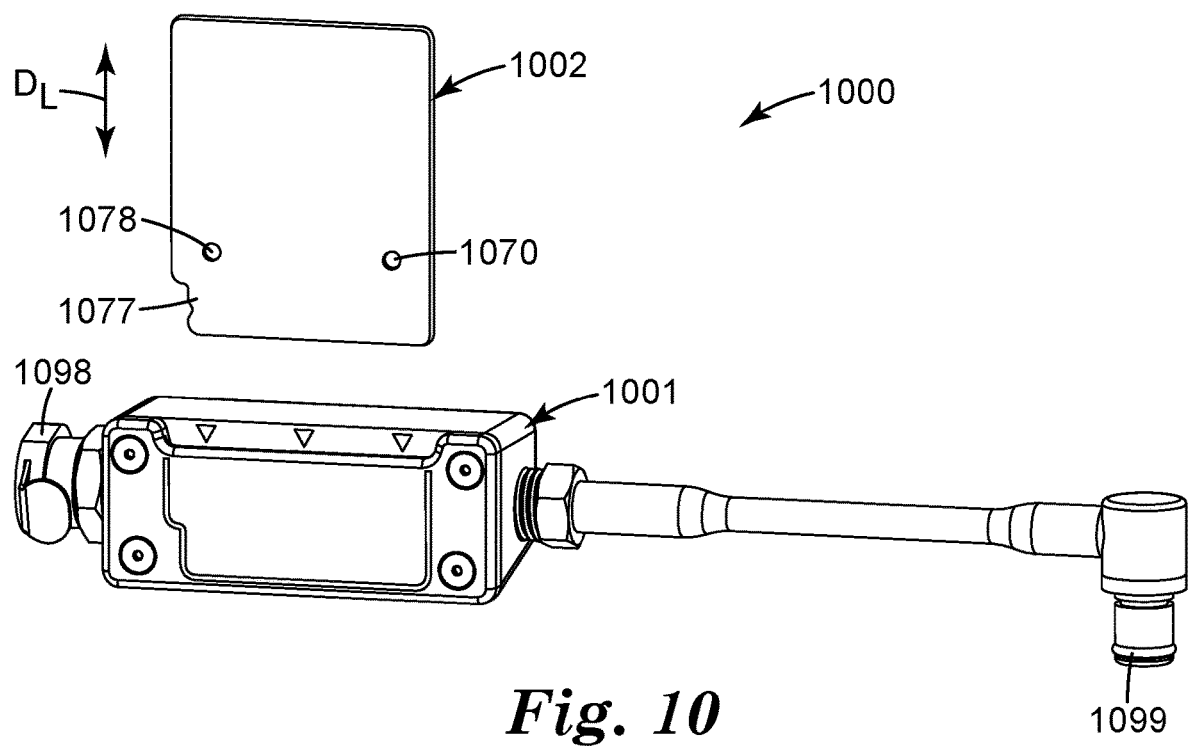
FIG. 10 is front perspective view of a microbial indicator device and an adaptor.
Figure 11:
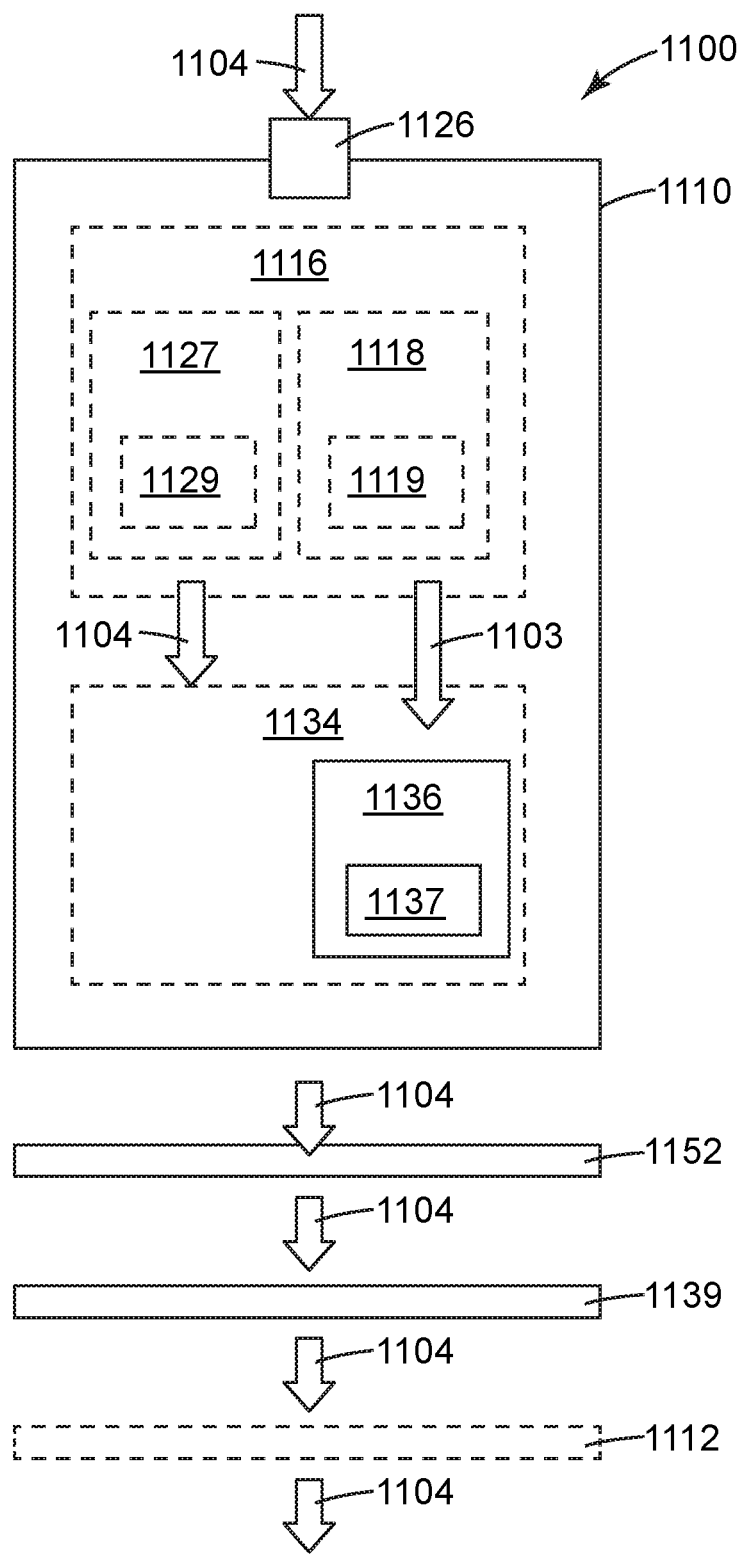
FIG. 11 is a block diagram of a microbial indicator device.

FIG. 11 provides a block diagram of a microbial indicator device 1100. The microbial indicator device 1100 depicted in FIG. 11 is a functional diagram and it is understood that features are not necessarily to scale or function. The numbering of components in microbial indicator device 1100 can be similar to that of other embodiments of microbial indicator devices. For example, microbial indicator devices in FIGS. 1-10 or FIGS. 12-16. Although a general direction of flow is implied, nothing in this section is meant to convey a particular order of fluid flow. The microbial indicator device 1100 can have a first housing 1110 and an optional second housing 1112. An aspect of the microbial indicator device 1100 is that the microbial indicator device can be configured to receive a disinfectant that flows from a reprocessing system (which may be referred to as a second fluidic path 1104). The microbial indicator device 1100 can also be configured to house a source of biological activity 1137 (e.g., vegetative organisms, yeast) which is activated by a liquid 1119 (e.g., an aqueous fluid or liquid medium) if a disinfection process is ineffective. The flow of the liquid 1119 to the source of biological activity 1137 can occur at least partially within the first housing 1110 and can be referred to as a first fluidic path 1103. The first housing 1110 can contact at least one of the fluidic paths 1103, 1104.

In some embodiments, the first housing can optionally house a separate container 1127 with a dry nutrient powder 1129. For example, the container 1127 can be frangible or dissolvable in the liquid 1119. In some embodiments, the container 1127 can be a tablet that dissolves partially upon a certain flow rate of disinfectant and releases the dry nutrient powder 1129 upon a water cycle of an AER. The dry nutrient powder 1129 can combine with the source of biological activity 1137. When wetted, the dry nutrient powder 1129 can form a liquid medium 1119.

The first housing 1110 or second housing 1112 can be made from relatively impervious materials to aqueous liquids. For example, suitable materials for the first housing 1110 can include, but are not limited to, a glass, a metal (e.g., foil), a polymer (e.g., polycarbonate (PC), polypropylene (PP), polyphenylene (PPE), polythyene, polystyrene (PS), polyester (e.g., polyethylene terephthalate (PET)), polymethyl methacrylate (PMMA or acrylic), acrylonitrile butadiene styrene (ABS), cyclo olefin polymer (COP), cyclo olefin copolymer (COC), polysulfone (PSU), polyethersulfone (PES), polyetherimide (PEI), polybutyleneterephthalate (PBT)), a ceramic, a porcelain, or combinations thereof.

The first housing 1110 can receive a disinfectant via the second fluidic path 1104. The second fluidic path 1104 can enter the first housing 1110 through a first coupling portion 1126. The second fluidic path 1104 can optionally contact a container 1118 containing the liquid 1119.

The second fluidic path 1104 contacts the source of biological activity 1137 (described further herein). For ease of use, the source of biological activity 1137 can be placed on a carrier 1136 (described herein). The second fluidic path 1104 can further contact a filter membrane 1152. An aspect of the present disclosure is that the filter membrane 1152 prevents at least some of the source of biological activity 1137 from exiting the microbial indicator device 1100.

The filter membrane 1152 can have an effective porosity sufficient to prevent at least some of the sources of biological activity 1137 from exiting the microbial indicator device without causing significant backpressure (e.g., pressure out should be no greater than 90% of the pressure in, or greater than a 10% pressure differential would result in significant backpressure). The backpressure can be balanced by controlling the resistance to flow of the internal channels (e.g., the first coupling portion, the source of biological activity 1137, any tortuous path) relative to the resistance to flow of the filter membrane 1152. The resistance to flow of the filter membrane 1152 is no greater than that of the resistance to flow of the internal channels.

Upon passing through the filter membrane 1152, the second fluidic path 1104 can pass through the second side of the filter membrane 1139 (which may also be referred to as an outlet). An outlet may be indicated by a physical partition or can be a second side 1139 of the filter membrane 1152. Further adapting means can be provided by the second housing 1112 to connect to a reprocessing system.

The first fluidic path 1103 is defined by the path from a liquid 1119 in a second state of an optional container 1118 (described further herein) to the source of biological activity 1137. If the disinfection process was effective, meaning that a certain number of microorganisms were killed/deactivated, then the source of biological activity 1137 does not produce a positive indication when exposed to the liquid for a predetermined length of time (e.g., 1 hour). If the disinfection process was not effective, then the source of biological activity 1137 produces a positive indication when exposed to the liquid for a predetermined amount of time (e.g., 1 hour).

The liquid 1119 does not necessarily have to originate from a container 1118 (as in a self-contained indicator) but can also enter through the first coupling portion 1126. Following the first fluidic path 1103, the liquid 1119 can interact with the source of biological activity 1137.

Although depicted as optional, cavities 1116 and 1134 can be effective at securing or directing fluid to or from the container 1118, carrier 1136, or the source of biological activity 1137. Any raised portion from a major surface can form a cavity (such as 1116 and 1134) and is not limited to only depressed portions.

An aspect of the present disclosure is that there is minimal pressure differential between the first coupling portion 1126 and the second side 1139 of the filter membrane 1152. For instance, when a disinfectant is received at the first coupling portion 1126 at a first pressure at 25 degrees C., and the disinfectant exits the second side 1139 at a second pressure at 25 degrees C., then the second pressure is at least 90 percent of the first pressure.

FIG. 1 provides a microbial indicator device 100 of the present disclosure. The microbial indicator device 100 can have a first housing 110 and optional second housing 112.

Generally, the first housing 110 can include various channels and cavities for producing both a tortuous fluidic path for a disinfectant and a fluidic path for a liquid (e.g., medium) for a microbial indicator. The second housing 112 can provide secure a filter membrane (described herein) to the first housing 110. In some embodiments, the filter membrane can couple with the first housing 110 and also form a hermetic seal with a portion of the first housing 110. The second housing 112 can also provide an interface for an input and output to mate with that of an adaptor for an AER. It should be understood that a one-part unitary housing may also be employed or that the first and second housings 110 and 112 can take on other shapes, dimensions, or relative structures without departing from the spirit and scope of the present disclosure.

The first housing 110 can be defined by at least one liquid impermeable major surface, such as the first major surface 111 and one or more side portions 114.

The side portions 114 can be adjacent to the filter membrane 152 and the first housing 110. In some embodiments, the side portions 114 can be configured such that the microbial indicator device 100 can fit into an adaptor.

The first major surface 111 can have a plurality of cavities including a first cavity 116 and a second cavity 134. Generally, the first cavity 116 can be configured to hold a container 118 filled with a liquid 119 (e.g., a nutrient medium). The second cavity 134 can be configured to hold a carrier 136 containing a source of biological activity 137. For example, the carrier 136 can have the source of biological activity 137 disposed thereon. The liquid 119 can cause the source of biological activity 137 to produce a visual indication of disinfection.

At least a portion of the first cavity 116 is defined by a recessed portion on the first major surface 111 of the first housing 110 to allow the first major surface 111 to be generally planar. The first cavity 116 has a sufficient volume to hold a container 118. At least a portion of the container 118 is frangible. In some embodiments, the frangible container 118 can contain a liquid (e.g., an aqueous mixture) 119. The liquid 119 can be of a volume sufficient to be received within the microbial indicator device 100. For example, a second cavity 134 can have a sufficient volume to contain a volume of the liquid 119).

The frangible container 118 can be formed of a variety of materials, including, but not limited to, one or more of metal (e.g., foil), a polymer (e.g., any of the polymers listed above with respect to the first housing 110), glass (e.g., a glass ampoule), and combinations thereof. In some embodiments, only a portion of the container 118 is frangible, for example, the container 118 can include a frangible portion or cover (e.g., a frangible barrier, film, membrane, or the like). In some embodiments, the frangible container 118 can be configured to facilitate fracturing of the frangible container 118 in a desired manner. For example, in some embodiments, a portion of the frangible container 118 can be formed of a thinner and/or weaker material, such that the portion preferentially fractures over another portion of the frangible container 118. In addition, in some embodiments, the frangible container 118 can include a variety of features positioned to facilitate fracturing of the frangible container 118 in a desired manner, including, but not limited to, a thin and/or weakened area, a score line, a perforation, or the like, or combinations thereof.

The container 118 can have a first state in which the container is intact and the liquid 119 is not in fluid communication with an interior of the first cavity 116 and a second state in which the container 118 is fractured and the liquid 119 is in fluid communication with the first cavity 116. In some embodiments, the frangible container 118 can have a first closed state in which the liquid 119 is contained within the frangible container 118 and a second open state in which the frangible container 118 has fractured and the liquid 119 is released into the second cavity 134, and in fluid communication with the carrier 136 containing a source of biological activity 137.

In some embodiments, the liquid 119 can include a nutrient medium for the source of biological activity (e.g., vegetative organisms), such as a germination medium that will promote germination of surviving microorganisms. In some embodiments, the liquid 119 can include water (or another solvent) that can be combined with nutrients to form a nutrient medium. The source of biological activity is configured to be activated by the liquid 119 meaning that the source of biological activity 137 produces a visual indication after a period of time if the disinfection cycle is not adequate.

Suitable nutrients can include nutrients necessary to promote germination and/or growth of surviving sources of biological activity (e.g., vegetative organisms) and may be provided in a dry form (e.g., powdered form, tablet form, caplet form, capsule form, a film or coating, entrapped in a bead or other carrier, another suitable shape or configuration, or a combination thereof) in the second cavity 134, for example, in the carrier 136 containing a source of biological activity 137. The liquid 119 can combine with the dry media to activate the source of biological activity 137.

Nutrient medium used to nourish the sources of biological activity (e.g., vegetative organisms) following a disinfection procedure can be present throughout the disinfection procedure but may not be accessible by the sources of biological activity until desired. For example, a frangible pouch or container 118 (e.g., an ampoule, such as a glass ampoule) can house the medium 'on board' separately from the sources of biological activity, and the container can be fractured to put the sources of biological activity and medium in fluid communication with one another, when desired (e.g., after a disinfection process). Nutrients and nutrient media to facilitate the growth of microorganisms are known in the art and can be found, for example, in the "Handbook of Microbiological Media" by Ronald Atlas, published by CRC Press, Boca Raton, Fla. Examples of nutrient media are aqueous solutions of soybean-casein digest broth, agar, urea, fluid thioglycollate and Dextrose Tryptone (Difco Laboratories, Inc.) A modified tryptic soy broth base, without glucose, can also be prepared.

The nutrient medium or liquid 119 can generally be selected to induce germination and initial outgrowth of the source of biological activity (e.g., vegetative organisms), if viable. The nutrient medium can include one or more sugars, including, but not limited to, glucose, fructose, cellibiose, or the like, or a combination thereof. The nutrient medium can also include a salt, including, but not limited to, potassium chloride, calcium chloride, or the like, or a combination thereof. In some embodiments, the nutrient medium can further include at least one amino acid, including, but not limited to, at least one of methionine, phenylalanine, and tryptophan.

In some embodiments, the nutrient medium can include indicator molecules or reagents, for example, indicator molecules having optical properties that change in response to germination or growth of the microorganisms. Suitable indicator molecules or reagents can include, but are not limited to, pH indicator molecules (e.g., bromocresol purple (BCP) as shown in the Examples, bromocresol green (BCG), chlorophenol red (CPR), bromothymol blue (BTB), bromophenol blue (BPB), other sulfonephthalein dyes, methyl red, or combinations thereof), enzyme substrates (e.g., 4-methylumbelliferyl-α-D-glucoside), DNA binding dyes, RNA binding dyes, other suitable indicator molecules, or a combination thereof.

In addition, in some embodiments, the liquid 119, either before or after coming into fluid communication with the source of biological activity (e.g., vegetative organisms), can include one or more inhibitors, or other components, that may interfere with an accurate assay or detection process. In some embodiments, examples of inhibitors can include at least one of dyes, indicator reagents, other materials or substances that may inhibit a reaction (e.g., an enzymatic reaction) necessary for detection of organism viability (e.g., salts, etc.), other materials or substances that may interfere with the detection process, or combinations thereof. In such embodiments, the carrier 136 containing a source of biological activity 137 can be configured to absorb and/or selectively concentrate one or more inhibitors from the liquid 119.

In some embodiments, carrier 136 promotes the immobilization of the source of biological activity (e.g., vegetative organisms) on the desired surface. In some embodiments, the carrier 136 is a nonwoven polymer and may further include a dry nutrient medium.

In some embodiments, the carrier 136 is made of an absorbent or a wicking material. For example, the wicking material can be positioned near the source of biological activity (e.g., vegetative organisms), can form at least a portion of or be coupled to a microorganism substrate, or the like, or a combination thereof. Such a wicking material can include a porous wicking pad, a soaking pad, or the like, or a combination thereof, to facilitate bringing the liquid 119 into intimate contact with the source of biological activity 137.

In some embodiments, the source of biological activity (e.g., vegetative organisms) are positioned (e.g. applied by coating or another application method) on a microstructured or microreplicated surface. For example, such a microstructured surface can be provided by an inner surface of the second cavity 134, can form a portion of or be coupled to a microorganism substrate, or the like, or a combination thereof.

Generally, sources of biological activity (e.g., vegetative organisms, or microorganisms) are chosen to be used in a biological indicator that are resistant to a particular disinfection process. The biological indicators of the present disclosure include a viable quantity, or culture, of one or more known sources of biological activity (e.g., species of microorganism). Such sources of biological activity can be in the form of microbial spores. The test source in the biological indicator is either killed by a successful disinfection cycle, or survives if the disinfection cycle is not adequate for some reason. Bacterial spores, rather than the vegetative form of the organisms, are sometimes used at least partly because vegetative bacteria are known to be relatively easily killed by sterilizing processes. Spores can also have superior storage characteristics and can remain in their dormant state for years.

By way of example only, the present disclosure describes the one or more sources of biological activity used in the biological indicator as being "microorganisms;" however, it should be understood that the type of source (e.g., spore) used in a particular embodiment of the biological indicator is selected for being highly resistant to the particular disinfection process contemplated. Accordingly, different embodiments of the present disclosure may use different sources of biological activity, depending on the disinfection process for which the particular embodiment is intended. The term "microorganisms" is used throughout the present disclosure for simplicity, but it should be understood that sources of biological activity, such as microorganisms (e.g., bacteria, fungi, viruses, etc.), spores (e.g., bacterial, fungal, etc.), enzymes, substrates for enzymatic activity, ATP, microbial metabolites, or a combination thereof, can be used in the biological indicator of the present disclosure instead.

The phrase "biological activity" generally refers to any specific catalytic process or groups of processes associated with a biological cell. Nonlimiting examples of biological activities include catabolic enzyme activities (e.g., carbohydrate fermentation pathways), anabolic enzyme activities (e.g., nucleic acid, amino acid, or protein synthesis), coupled reactions (e.g., a metabolic pathway), biomolecule-mediated redox reactions (e.g., electron transport systems), and bioluminescent reactions.

It may be possible to use spores or weakened/injured spores as the source of biological activity 137 in a liquid sterilization indicator. As mentioned above, one of the advantages of using spores in this application is that they are "shelf stable" for long times at room temperature. Germination and growth of the spores is not easily triggered except by design. In some embodiments, it may be possible to simply measure the amount of viable spores present after a reprocessing (e.g., disinfection) cycle and compare it to the predetermined amount of spores placed in a chamber of the cartridge. That difference in the spore population pre and post reprocessing could then be compared to an expected difference for an effective cycle, and within a certain tolerance window, a determination could be made on whether the reprocessing cycle was effective or not (i.e., pass or fail). The measured difference would also quantify the log reduction achieved during the cycle.

The process of bringing the microorganisms and medium together can be referred to as "activation" of the biological indicator. That is, the term "activation" and variations thereof, when used with respect to a biological indicator, can generally refer to bringing one or more sources of biological activity (e.g., vegetative organisms) in fluid communication with a liquid or medium (e.g., a nutrient medium for the microorganisms of interest). For example, when a frangible container within the biological indicator that contains the medium is at least partially fractured, punctured, pierced, crushed, cracked, or the like, such that the medium has been put in fluid communication with the source(s) of biological activity, the biological indicator can be described as having been "activated." Said another way, a biological indicator has been activated when the source(s) of biological activity have been exposed to the medium which was previously housed separately from the source(s) of biological activity.

The source of biological activity 137 of the present disclosure can be used with a variety of disinfection or liquid sterilization processes including, but not limited to, liquid agents (e.g., orthophthaldehyde (OPA), glutaraldehyde, a tertiary amine compound (TAC), hydrogen peroxide, peracetic acid, or combinations thereof). In at least some of the disinfection processes, an elevated temperature, for example, 20° C.-60° C. or the like, is included or may be encountered in the process. In addition, elevated pressures and/or a vacuum may be encountered, for example, 15 psi ($1 \times 10^5$ Pa).

Although several sources of biological activity 137 are possible, a few species are preferable for high-level disinfection. For example, the U.S. Food and Drug Administration (FDA) recognizes a high-level disinfection as achieves a 6-log reduction of a mixed suspension of vegetative organisms, such as *Pseudomonas aeruginosa, Staphylococcus aureus, Escherichia coli*, and representatives of the *Klebsiella-Enterobacter* group and a 6-log reduction of an appropriate *mycobacterium* species or equivalent species. For thermal disinfection processes, FDA recommends the use of a thermophilic *mycobacterium* species.

The high-level disinfection is distinguished from an intermediate-level disinfection in that the intermediate level disinfection achieves a 6-log reduction of the mixed suspension of vegetative organisms and a 3-log reduction of an appropriate *mycobacterium* species or equivalent species.

The high-level disinfection is distinguished from a low-level disinfection in that the low-level disinfection achieves a 6-log reduction of a mixed suspension of vegetative organisms, such as *Pseudomonas aeruginosa, Staphylococcus aureus, Escherichia coli*, and representatives of the *Klebsiella-Enterobacter* group.

As mentioned above, the sources of biological activity used in a particular system are selected according to the liquid sterilization or disinfection process used. The source of biological activity can be a bacterial spore if a liquid sterilization process is used. In some embodiments, process resistant spores can include, but are not limited to, at least one of *Geobacillus stearothermophilus, Bacillus stearothermophilus, Bacillus subtilis, Bacillus atrophaeus, Bacillus megaterium, Bacillus coagulans, Clostridium sporogenes, Bacillus pumilus*, or combinations thereof.

If bacterial spores were found to be too resistant to be affected by the reprocessing cycle (e.g., by the disinfectant used in AERs), another potential biological entity useful in this indication could be an appropriate yeast. For example, *Saccharomyces cerevisiae* is a species of yeast that could be employed in this concept. It is a yeast cell instrumental to winemaking, baking, and brewing and it is one of the most intensively studied eukaryotic model organisms in molecular and cell biology. In other examples, *Aspergillus brasiliensis* (formerly *Aspergillus niger*), or, can be used. Rapid detection of the biological indication could be achieved using a florescence based enzymatic reaction. Glucosidase assays using fluorogenic substrates are one such class. For example, β-Glucosidase catalyzes the breakdown of the β-glucosidic linkage in the fluorogenic substrate, β-4-methylumbelliferyl-beta-D-glucuronide, to release its component moieties glucose and the fluorescent compound 4-methylumbelliferone. The activity of this enzyme can then be measured as an increase in fluorescence over time from germinated spore suspensions. The reaction is potentially quantitative and could be used to determine the difference from a predetermined initial spore population prior to the initiation of a reprocessing cycle to a final spore population upon completion of the cycle.

Mycobacteria can also be used. Examples of mycobacteria that may be used may include *Mycobacterium chelonae, Mycobacterium gordonae. Mycobacterium smegmantis, Mycobacterium terrae, Mycobacterium bovis, Mycobacterium tuberculosis*, and the like.

Suitable enzymes can include hydrolytic enzymes and/or enzymes derived from spore-forming microorganisms, such as *Bacillus stearothermophilus* and *Bacillus subtilis*. Enzymes from spore-forming microorganisms that can be useful in the biological indicators of the present disclosure can include beta-D-glucosidase, alpha-D-glucosidase, alkaline phosphatase, acid phosphatase, butyrate esterase, caprylate esterase lipase, myristate lipase, leucine aminopeptidase, valine aminopeptidase, chymotrypsin, phosphohydrolase, alpha-D-galactosidase, beta-D-galactosidase, tyrosine aminopeptidase, phenylalanine aminopeptidase, beta-D-glucuronidase, alpha-L-arabinofuranosidase, N-acetyl-beta-glucosaminodase, beta-D-cellobiosidase, alanine aminopeptidase, proline aminopeptidase and fatty acid esterases.

Some embodiments of the biological indicator can include chromogenic and/or fluorogenic substrates that react with enzymes to form detectable products (M. Roth, *Methods of Biochemical Analysis, Vol.* 17, D. Block, Ed., Interscience Publishers, New York, 1969, p. 89, incorporated herein by reference; S. Udenfriend, *Fluorescence Assay in Biology and Medicine*, Academic Press, New York, 1962, p. 312; and D. J. R. Lawrence, *Fluorescence Techniques for the Enzymologist*, Methods in Enzymology, Vol. 4, S. P. Colowick and N. O. Kaplan, Eds., Academic Press, New York, 1957, p. 174). These substrates may be classified in two groups based on the manner in which they create a visually detectable signal or product. The substrates in the first group react with enzymes to form enzyme-modified products that are themselves chromogenic or fluorescent. Substrates in the second group form enzyme-modified products that must react further with an additional compound, or compounds, to create a detectable product that can generate a color or fluorescent signal.

As a result, the phrase "detectable product" can refer to any molecule, compound, substance, substrate, or the like, or combinations thereof, that can be detected by any of the detection methods or processes described below. For example, such detectable products can be a sign of the viability of a source of biological activity, and detection of such products can generally indicate the failure or inadequacy of a disinfection process.

The second cavity 134 is fluidically coupled to the first cavity 116 via a first fluidic path. The first fluid path can be a path taken by the liquid 119 to get to the second cavity 134. In some embodiments, the first fluidic path can be direct with the first cavity 116 coupling directly with the second cavity 134. An optional microfluidic channel 121 within the first major surface 111 can also indirectly couple the first cavity 116 and the second cavity 134 (via the funneling cavity 120 and a portion of channel 133). The microfluidic channel 121 can be a recessed portion of the first major surface 111. If the optional microfluidic channel 121 is present, then the second drain passage 124 (formed from the first housing 110) can be absent (thus sealed).

In other embodiments, the first fluidic path can be circuitous and the first fluidic path (discussed herein) can include first drain passage 138, second drain passage 124 and the funneling cavity 120.

The second cavity 134 can further include a modified inner surface, such as a reflective surface, a white surface, a black surface, or another surface modification suitable to optimize the optical properties of the surface. A reflective surface (e.g., provided by a metal foil) can be positioned to reflect a signal sent into the second cavity 134 from an assaying or detection device and/or to reflect any signal generated within the second cavity 134 back toward the assaying device. As a result, the reflective surface can function to improve (e.g., improve the intensity of) a signal from the microbial indicator device 100. Such a reflective surface can be provided by an inner surface of the second cavity 134; a material coupled to the inner surface of the second cavity 134 or the like; or the reflective surface can form a portion of or be coupled to a microorganism substrate; or a combination thereof.

The funneling cavity 120 can be optional and positioned adjacent to the first cavity 116. The funneling cavity 120 can be positioned within at least a portion of the first fluidic path. The funneling cavity 120 can direct the liquid 119 towards the second cavity 134 when the container 118 is in the second state. For example, when the orientation of the first housing 110 is positioned such that the first cavity 116 is situated above the first drain passage 124 and along a longitudinal axis $D_L$, then the liquid 119 can flow along the first fluidic path toward the second cavity 134. In some embodiments, the liquid 119 flows along the second major surface (not shown) of the first housing 110. The second major surface is described further herein.

Generally, the first cavity 116 can be oriented such that the liquid 119 flows from the first cavity 116 to the second cavity 134 using gravity (when the container 118 is in the second state). This means that when the first housing 110 is positioned such that a side portion 114 is parallel to a longitudinal axis $D_L$, the liquid 119 flows in a downward direction. When the container 118 is in the second state, the top of the microbial indicator device 100 (marked by the container 118) is above the second cavity 134 along the longitudinal axis.

A portion of the funneling cavity 120 can be defined by a recessed portion on the first major surface 111 of the first housing 110. The recessed portion can direct the liquid 119 toward the first drain passage 124 which may be situated closer to the first major surface than the beginning of the first fluidic path of the funneling cavity 120. The funneling cavity 120 can also have raised portions 122 that can further direct the liquid 119 into the first drain passage 124.

The first drain passage 124 goes through the housing 110 and connects the first major surface 111 with the second major surface (not shown). The first drain passage is fluidically coupled with the second cavity 134 and the first cavity 116. The first drain passage 124 can also be fluidically coupled with the funneling cavity 120 and the first filter cavity (not shown).

A second drain passage 138 can exist between the first major surface 111 and the second major surface of the first housing 110. The second drain passage 138 can facilitate movement of liquid 119 from the first cavity 116 to the second cavity 134. The second drain passage 138 can be shaped with a narrowing portion to direct liquid 119 into the second cavity 134 using capillary forces. Thus, the second drain passage 138 can be fluidically coupled with the second cavity 134 and the first cavity 116. The second drain passage 138 can also be fluidically coupled with the second cavity 134 and the first filter cavity 156 (shown in FIG. 7).

The first fluidic path can also include a vent 142 to facilitate movement of the liquid 119 into the second cavity 134. In some embodiments, the facilitated liquid 119 flows through and/or within the microbial indicator device 100 can be provided by employing one or more vents 142 or vent channels 140 (which may be referred to as a third channel). Such vents 142 can be provided by fluid paths that are formed within the biological indicator. The phrases "vent," "internal vent," "vent channel," or variations thereof can generally refer to a fluid path that is positioned to allow gas present in one region (e.g., chamber, reservoir, volume, portion, etc.) of the microbial indicator device to be displaced when another fluid (e.g., a liquid, a gas or combinations thereof) is moved into that region. Particularly, such phrases generally refer to internal fluid paths that allow one region within the microbial indicator device to be vented to another region within the microbial indicator device (e.g., when the microbial indicator device is enclosed) to facilitate fluid movement into a desired region of the microbial indicator device. Furthermore, such venting within the microbial indicator device can facilitate moving liquid 119 from a larger region (i.e., the first cavity 116) to a smaller region (e.g., the second cavity 134) of the microbial indicator device, particularly when the volume of liquid 119 to be moved is greater than the volume of the smaller region. In some embodiments, such internal venting 142 can facilitate fluid flow within or throughout the microbial indicator device 100 even without employing substantial, or any, external force, such as centrifugation, shaking, tapping, or the like.

The vent 142 can be coupled to the second cavity 134 via a vent channel 140. In some embodiments, the vent 142 is a passage that connects the first major surface 111 to the second major surface. The vent 142 can allow the displaced fluid to expand into an internal cavity of the microbial indicator device 100. In other embodiments, the vent 142 can allow the displaced fluid to expand into the atmosphere.

A portion of the vent 142 or vent channel 140 can be defined by a recessed portion on the first major surface 111 of the first housing. The vent 142 can be of a particular size relative to the second cavity 134. For example, the vent 142 can have an opening with a particular opening area. The second cavity 134 can have a second cavity cross-sectional area defined by the first major surface 111 plane. In some embodiments, the opening area is no greater than the second cavity cross-sectional area.

The first housing 110 can also accommodate a second fluidic path. The second fluidic path is the path of a liquid disinfectant caused by components of the first housing 110. The second fluidic path can include a channel 126 from a reprocessing system through the microbial indicator to a second coupling portion back to the reprocessing system.

The channel 126 can receive disinfectant from a reprocessing system and the second coupling portion can transport the disinfectant from the microbial indicator device 100 to the reprocessing system. The second fluidic path can be designed in a tortuous path to mimic the geometry of an endoscope. The second fluidic path is at least partially housed in the first housing 110, specifically the first major surface 111. The second cavity 134 can be positioned in the second fluidic path.

The second fluidic path can have at least one microfluidic channel (e.g., 128) following a tortuous path that is designed to mimic a full length flexible endoscope. For example, the arcuate path of the microfluidic channel is designed to mimic a full length flexible endoscope on the basis of Poiseuille's law. In the case of laminar flow, the volume flowrate is given by the pressure difference divided by the viscous resistance. This resistance depends linearly upon the viscosity and the length, but the fourth power dependence upon the radius is dramatically different. Poiseuille's law is found to be in reasonable agreement with experiment for uniform liquids (Newtonian fluids) in cases where there is no appreciable turbulence.

According to Poiseuille's law, the volumetric flowrate can be given by:

$$\text{Volumetric Flowrate} = \mathcal{F} = \frac{P_1 - P_2}{\mathcal{R}} = \frac{\pi(P_1 - P_2)r^4}{8\eta L}$$

Where the resistance to flow $\mathcal{R}$ is given by:

$$\mathcal{R} = \frac{8\eta L}{\pi r^4}$$

Where $\eta$ is the viscosity of the liquid (at 25 degrees C.).

This advantageously allows mimicking the challenge posed to an AER by a flexible endoscope using a considerably condensed format. For example, some of the larger gastrointestinal flexible endoscopes have 2 m long lumens 5 mm in diameter. Given a disinfectant with a known viscosity $\eta$, the resistance to flow $\mathcal{R}$ will be proportional to $L/r^4$, which for the example is equal to 51.2 $\text{mm}^{-3}$. In other embodiments, the resistance to flow can be between 50 $\text{mm}^{-3}$ to 8000 $\text{mm}^{-3}$ inclusive, or preferably 50 $\text{mm}^{-3}$ to 1600 $\text{mm}^{-3}$. To simulate an equivalent resistance using a microfluidic channel 1 mm in diameter, the length L necessary would be only 3.2 mm.

A portion of a microfluidic channel 128 that defines a portion of the second fluidic path is further defined by a recessed portion on the first major surface of the first housing. In some embodiments, the majority of the second fluidic path is defined by a recessed portion on the first major surface of the first housing.

In the following example, the second fluidic path is provided by channel 126, channel 128, a third cavity 130, channel 133, the second cavity 134, and the second drain passage 138 leading to a liquid outlet (not shown).

The third cavity 130 can be positioned within the second fluidic path. The third cavity 130 can be positioned within the first major surface 111 and formed from a recessed portion. The channel 128 can connect a channel 126 with the third cavity 130. The channel 128 can form a process challenge through a tortuous path.

The third cavity 130 can be configured to house a chemical indicator 132 that indicates whether a disinfection process results in sufficient disinfection.

The chemical indicator 132 can include various types. For example, suitable chemical indicators for use with the devices described herein would comprise a colorimetric system to verify the minimum effective concentration (MEC) of disinfectant liquid.

One possible system would be based on the reaction of a commonly used high level disinfectant, ortho-phthalaldehyde with sodium sulfite disposed on a substrate. The reaction forms a sulfite addition product and an equivalent amount of base according to the following reaction:

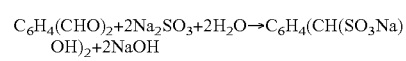

If sufficient ortho-phthalaldehyde is present, the increase in pH causes a color change in the pH indicator also disposed on the substrate. When the concentration of ortho-phthalaldehyde is sufficient, the local pH typically rises above 11 and a color change to a deep purple occurs. There are several suitable pH dyes that can be used in this indication. A similar reaction scheme can be used to test MEC for glutaraldehyde (GA) disinfectants, another common class of HLD (High Level Disinfection) chemicals used in reprocessing flexible endoscopes. The chemical indication could be also configured to be an integrator, meaning that it will measure not just whether the disinfectant is above a certain concentration but for how long it was at that concentration. This could be done by providing an indicator system where the colorimetric response was proportional to a dosage or contact time. For example, by disposing the indicator system along a wicking strip rather than in a dot, and allowing for capillary action in the wicking material to dictate the flow of disinfectant along the strip, visualization of the colorimetric front along the strip would then become an indication of time as well as MEC. The porosity of the strip would be chosen to achieve the desired movement of disinfectant along the strip for a given cycle duration. The wicking strip could be made of an appropriate membrane or filtration material but it could also be engineered as an additional microfluidic component that forms a monolithic structure along with the challenge channel of the device.

Figure 2:
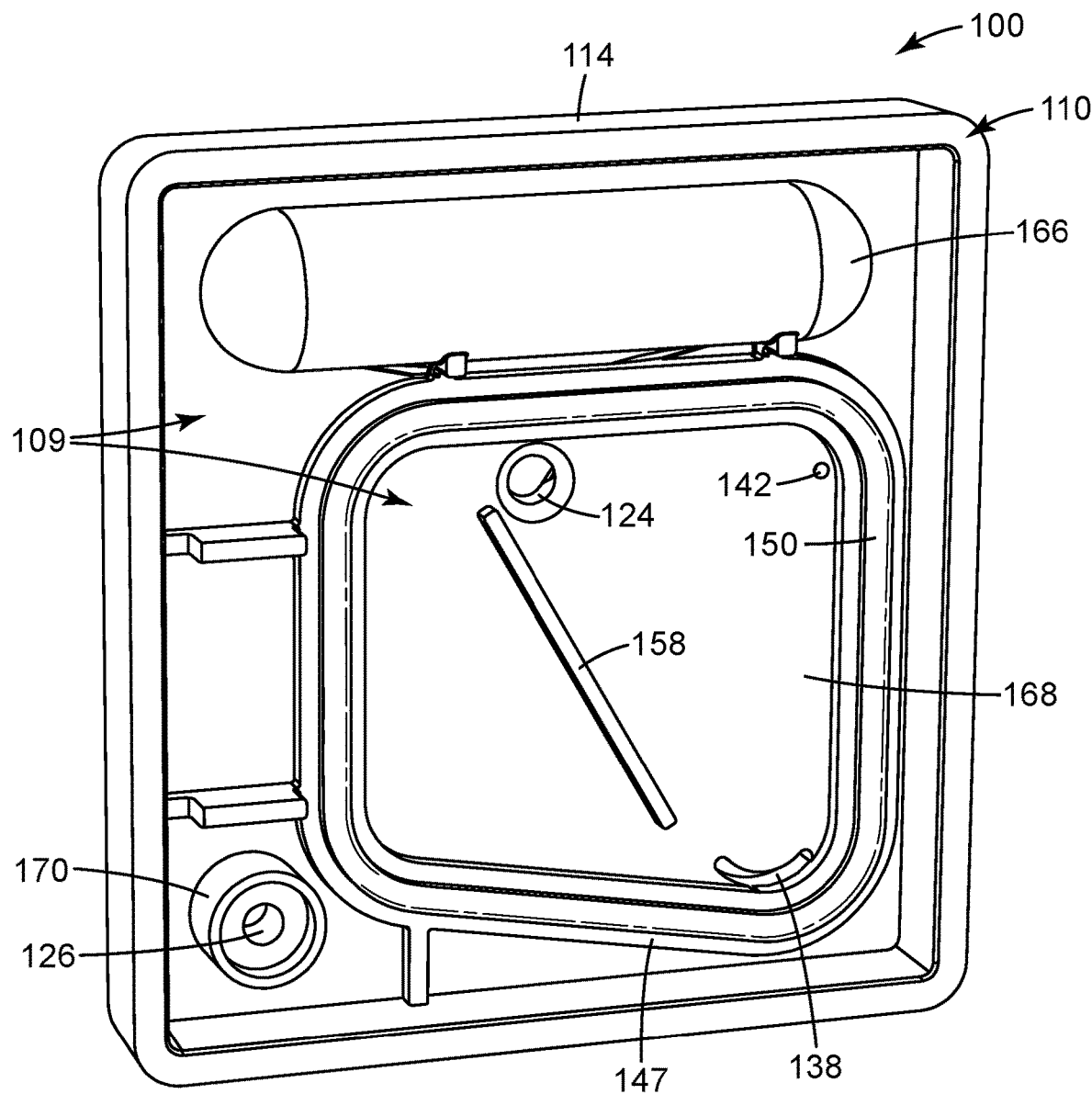
FIG. 2 is a rear perspective view of the first housing of a microbial indicator device of FIG. 1.

In FIG. 2, the backside or second major surface 109 of first housing 110 is shown. The second major surface 109 can include one or more raised portions. For example, raised portion 166 can be the corresponding opposite surface from the first cavity 116 in FIG. 1. Other features include the channel 126 which is reinforced by the coupling portion 170. The coupling portion 170 provide further securement means to the second housing 112. In some embodiments, the coupling portion 170 can secure an inlet from a reprocessing system for disinfectant to flow through the microbial indicator device.

The raised portion 147 can provide the boundaries of a sealing element 150. For example, the raised portion 147 can ensure that the sealing element 150 stays in place. In some embodiments, the raised portion 147 can have a recessed circular portion to better position the sealing element 150. The raised portion 147 can have a variety of shapes depending on the shape of the sealing element. In the following example, the raised portion 147 is trapezoidal such that liquid 119 entering from the first drain passage 124 can be diverted toward the second drain passage 138 and into the second cavity 134 (when the microbial indicator device 100 is upright, meaning that the top is above the bottom when oriented along the longitudinal axis).

The sealing element 150 functionally provides a seal between two surfaces. The term fluidic seal can refer to a seal that will not let water in or out at standard temperature and pressure. Seal and fluidic seal can be used interchangeably. In some embodiments, the sealing element 150 can provide a hermetic seal between the filter membrane 152 and the first housing 110 or second housing 112. A sealing element can be an o-ring, washer, adhesive, filler, putty, that is capable of forming a seal.

Within the boundaries of the raised portion 147, the second major surface 109 can have a first raised diverter portion 158 that is configured to align with a second raised diverter portion in the second housing. The sealing element 150 is considered optional and external to the first housing 110. For example, a filter membrane can be attached to the first housing 110 with an adhesive, negating the need for an sealing element.

Figure 3:
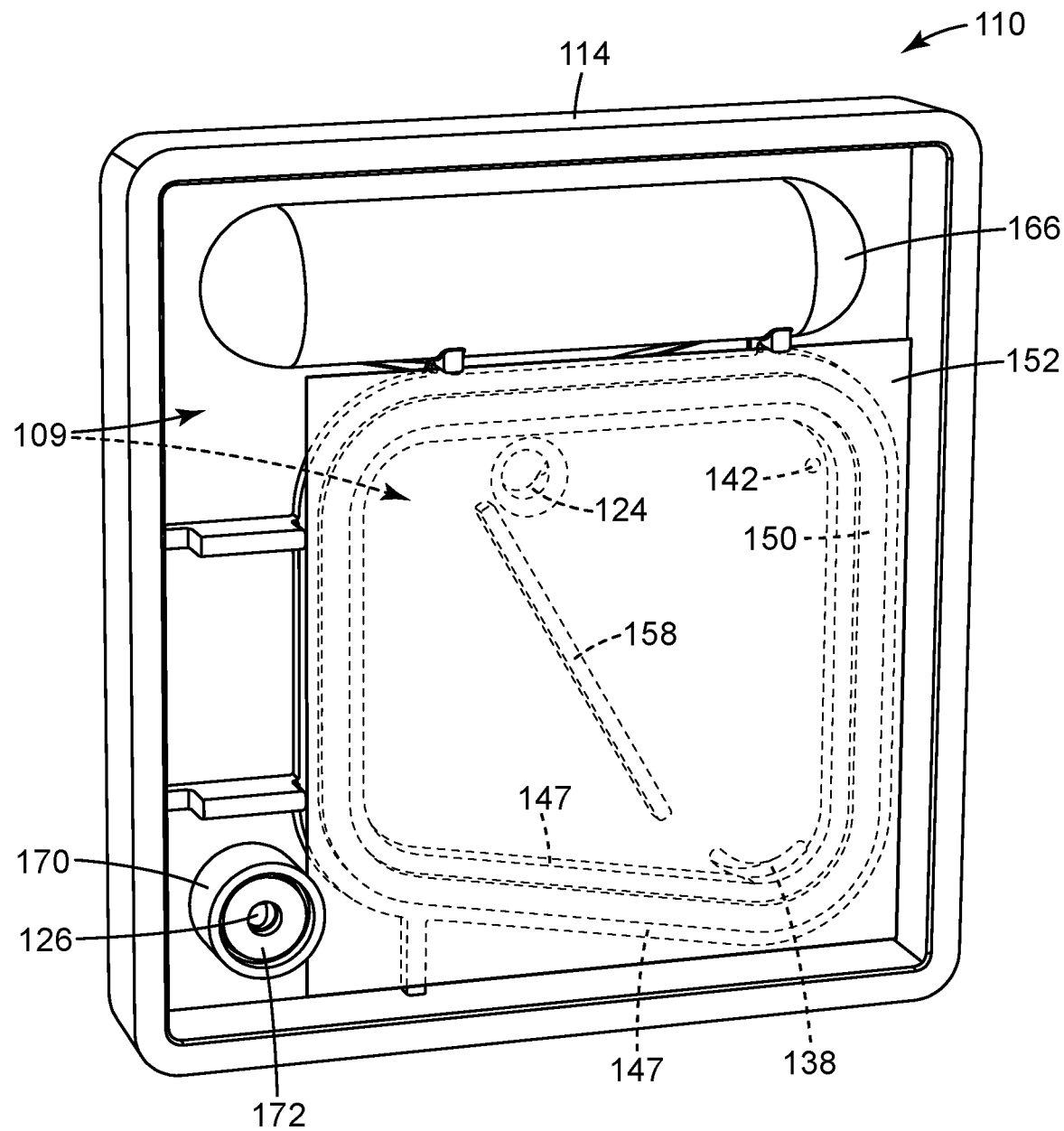
FIG. 3 is a rear perspective view of the first housing of a microbial indicator device of FIGS. 1-2 including a filter membrane and a one-way valve.

In FIG. 3, the filter membrane 152 and one-way valve 172 are provided as additional components. The filter membrane 152 is positioned in the second fluidic path such that a disinfectant flows from the second drain passage 138 through the filter membrane 152 before the fluid outlet is reached. The filter membrane 152 can be mostly two-dimensional, with the filter membrane 152 having a first side (toward the first housing 110) and a second side (opposite the first side). In some embodiments, a three-dimensional filter membrane can be used and positioned such that the surface area is increased on the first side toward the first housing (e.g., a funnel).

An aspect of the present disclosure is that the resistance to flow of the filter membrane 152 is no greater than the resistance to flow of the disinfectant within the process indicator device 100. Various sizes and geometries of the filter membrane can be used to lower the resistance to flow of the filter membrane. For example, porosity (e.g., pore size) can be modified and the surface area increased to reduce the resistance to flow of the filter membrane. Additionally, various internal channel dimensions (e.g., a tortuous path) can be used to modify the resistance to flow of the filter membrane.

The filter membrane 152 can have a pore size sufficient to retain at least a portion of the source of biological activity on the first side. For example, when disinfectant follows the second fluidic path, some of the sources of biological activity (e.g., vegetative organisms) may become dislodged from the carrier 136. An aspect of the present disclosure if that the filter membrane 152 prevents at least a portion of the sources of biological activity (e.g., vegetative organisms) from being introduced into the reprocessing system.

In some embodiments, the filter membrane 152 has an average pore size of no greater than 0.5 microns, no greater than 0.4 microns, no greater than 0.3 microns, no greater than 0.2 microns, no greater than 0.15 microns, no greater than 0.1 microns, and no greater than 0.05 microns.

Exemplary filter membranes 152 can be made by, for example, TIPS (thermally induced phase separation) process, SIPS (solvent induced phase separation) process, VIPS (vapor induced phase separation) process, stretching process, track-etching, or electrospinning (e.g., PAN fiber membranes). Suitable membrane materials include, for example, polyolefins (e.g., polyethylene and/or polypropylene), ethylene-chlorotrifluoroethylene copolymer, polyacrylonitrile, polycarbonate, polyester, polyamide, polysulfone, polyethersulfone, polyvinylidene fluoride (PVDF), cellulose ester, and/or combinations thereof.

Suitable membranes may be characterized as porous membranes or as nanofiber membranes. Nanofiber filter membranes can have the fiber diameter less than 5 μm such as, for example, less than 1 μm. Nanofiber membranes may be prepared from, for example, polyacrylonitrile, polyvinylidene fluoride, a cellulose ester, polyvinyl acetate, polyvinyl alcohol, polyvinyl butyral, and/or combinations thereof.

Certain TIPS polyolefin membranes can be prepared so that they possess a single, homogeneous zone of membrane structure, each zone having a different pore microstructure. In other cases, a TIPS membrane may be prepared as a multi-zone membrane that includes two or more zones, each zone having a different pore microstructure. A multi-zone TIPS membrane may contain distinct zones or, alternatively, may possess a transition zone between two otherwise distinct zones. For example, the pore size of the second side of the membrane 152 can be larger than the pore size of the first side of the membrane 152, or vice versa.

Exemplary filter membranes include membranes and methods for making exemplary filter membranes are described in, for example, in U.S. Pat. Nos. 4,539,256, 4,726,989, 4,867,881, 5,120,594, 5,260,360, International Patent Publication No. WO2010/078234, International Patent Publication No. WO2010/071764, U.S. Provisional Patent Application Ser. No. 61/351,441, entitled, "Coated Porous Materials," filed Jun. 4, 2010, and U.S. Provisional Patent Application Ser. No. 61/351,447, entitled, "Process for Making Coated Porous Materials," filed Jun. 4, 2010.

The first side of the filter membrane 152 is in fluid communication with the first fluidic path. In some embodiments, the filter membrane 152 forms a first filter cavity (pictured in FIG. 7) between the first side of the filter membrane and the second major surface 109 of the first housing 110.

The first filter cavity (pictured in FIG. 7) can be further defined by the raised portion 147 of the second major surface 109 of the first housing 110. The filter membrane 152 can be sandwiched between the first housing 110 and the second housing 112.

The filter membrane 152 can contact the sealing element 150 and a sealing element. The filter membrane 152 can have a filter membrane surface area that is defined by the raised portions 147 of the second major surface 109 of the first housing.

An aspect of the present disclosure is the ratio of the filter membrane surface area to inlet area. The inlet area is the actual area of the channel 126 (which would include the extra material of the one-way valve 172.) The inlet area can be measured planar from the second major surface 109. As discussed herein, the resistance of a filter membrane 152 can be no greater than the resistance of a tortuous path of a disinfectant provided by elements following the second fluidic path. A desired resistance of the filter membrane 152 can provided by the size which can be proportional to the inlet area. In some embodiments, the ratio of the filter membrane surface area to inlet area can be at least 5:1 at least 10:1, at least 25:1, at least 35:1, at least 50:1, at least 100:1, at least 500:1, at least 800:1, or even at least 5000:1.

In some embodiments, the filter membrane 152 can have a resistance of between 10-40 ml/min/psi, inclusive.

Figure 4A:
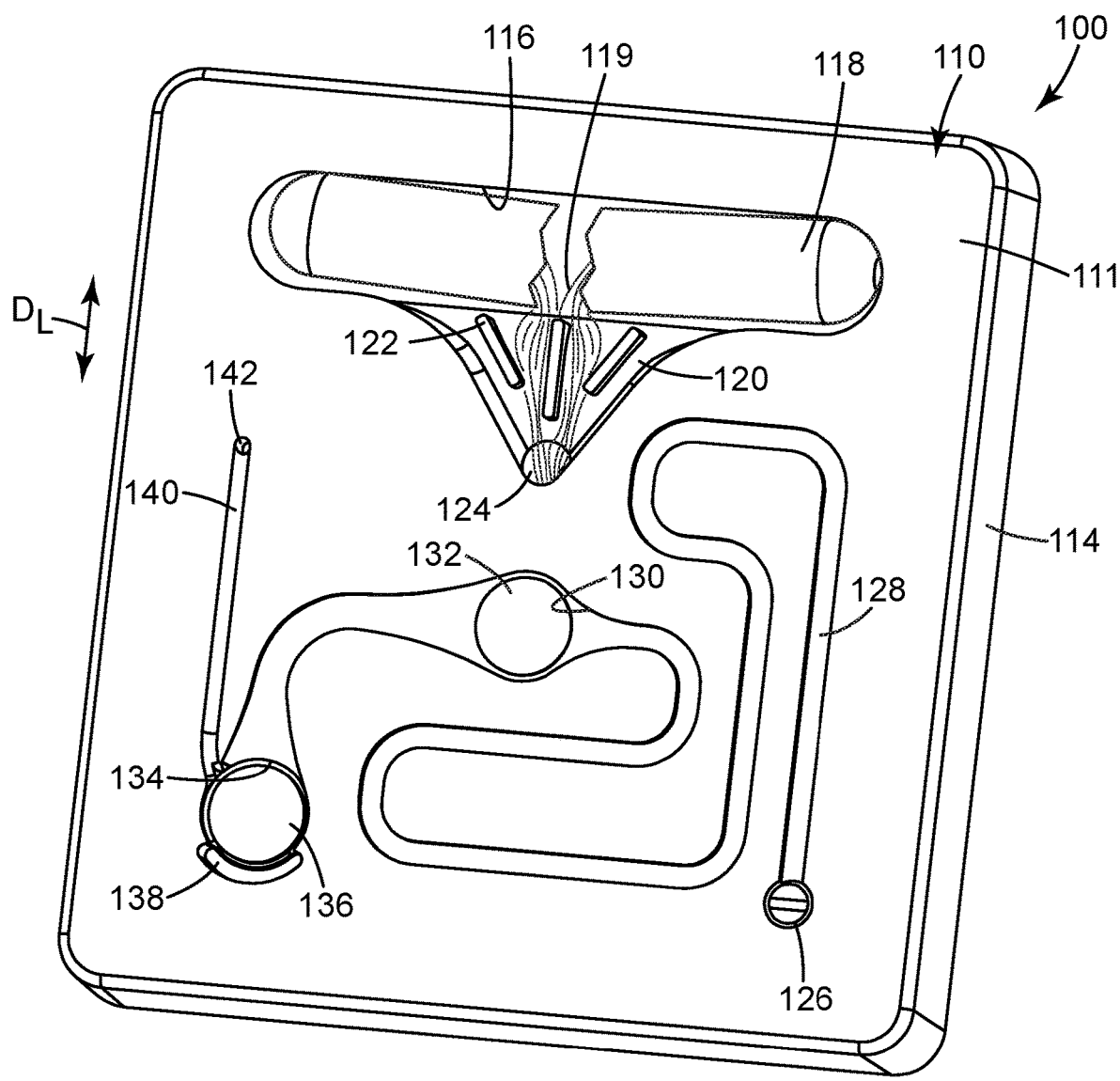
FIG. 4A is a front perspective view of the first housing of a microbial indicator device of FIGS. 1-3, a container of the microbial indicator device is shown in a second state.
Figure 4B:
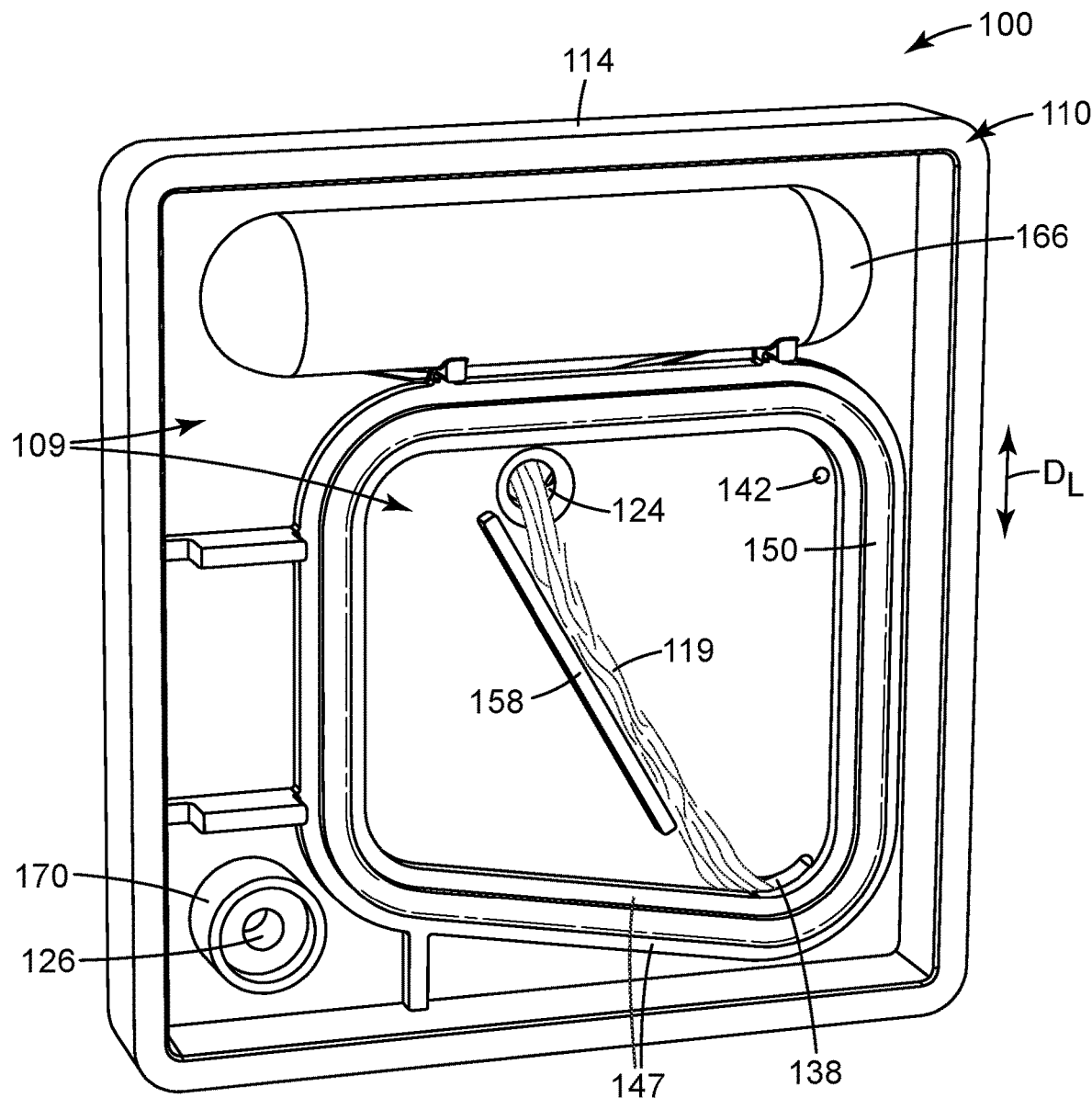
FIG. 4B is a rear perspective view of the first housing of the microbial indicator device of FIGS. 1-3, a container of the microbial indicator device is shown in a second state.

In FIG. 4A-4B, the first fluidic path is shown on the first major surface 111 and the second major surface 109.

In FIG. 4A, the container 118 is shown in a second state meaning that the container 118 is fractured. The liquid 119 flows through the funneling cavity 120 and is directed by raised portion 122 into the first drain passage 124.

In FIG. 4B, the liquid 119 emerges from the first drain passage 124 on the second major surface 109 and is directed by the first raised diverter portion 158 into the second drain passage 138. The liquid 119 is held in place by the filter membrane 152 which restricts the flow of liquid 119 from the second filter cavity. Thus, the liquid 119 is primarily restricted into the first filter cavity (not shown). The liquid 119 entering the second drain passage 138 emerges from the first major surface 111 in FIG. 4A and is directed into the second cavity 134 through capillary action or physical rotation of the microbial indicator device 100.

Figure 5:
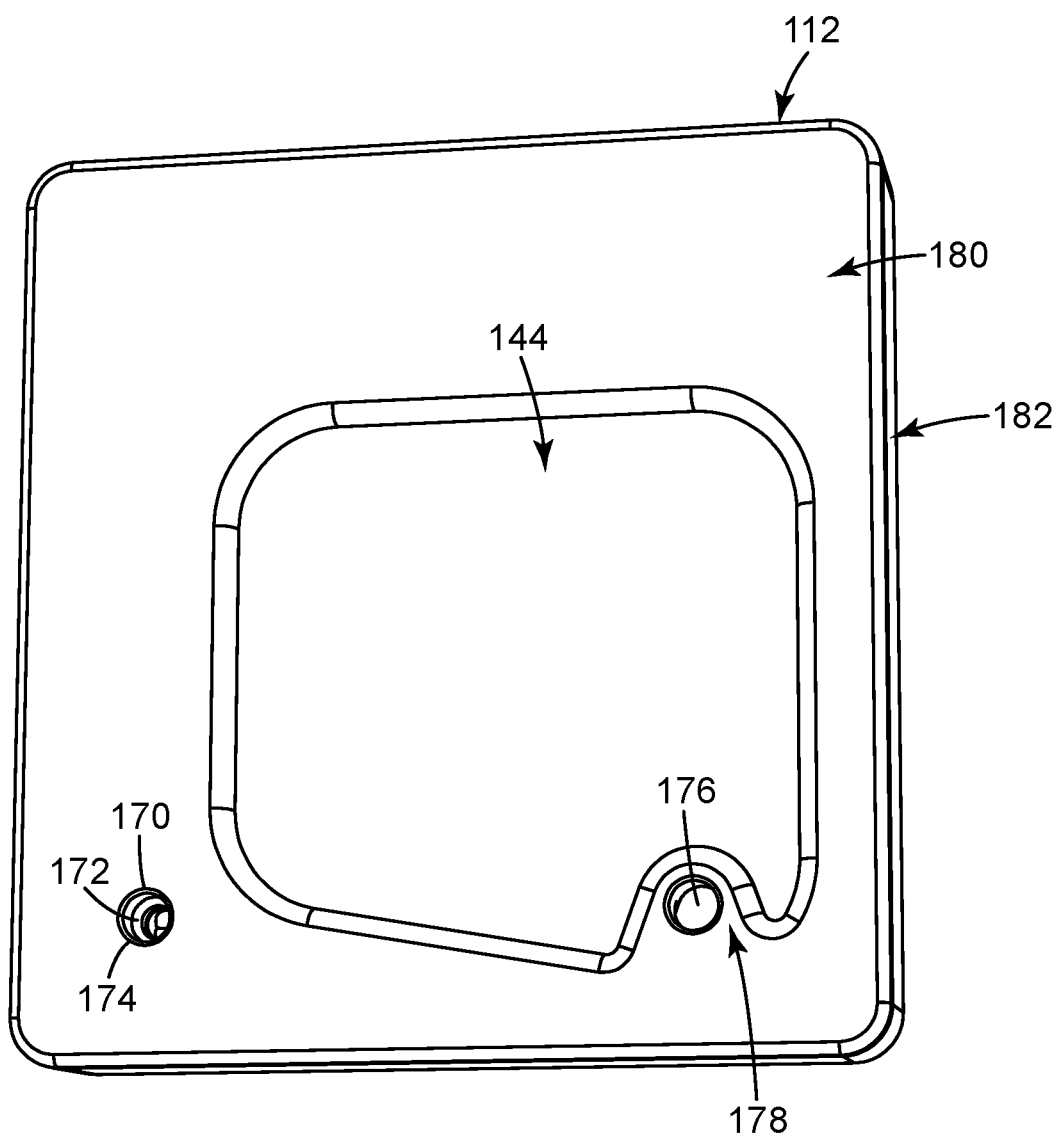
FIG. 5 is a front perspective view of the second housing of a microbial indicator device of FIG. 1.

In FIG. 5, the second housing 112 is shown in greater detail. The second housing 112 can be made from the same material as the first housing described herein. The second housing 112 can function as a cover plate and is configured to mate with the first housing 110 and optionally a harness adapter for a reprocessing system. The second housing 112 can have a first major surface 180, a second major surface (not shown), and one or more side portions 182.

The first major surface 180 can have a cut-out portion 174. The cut-out portion 174 can be configured to align with the coupling portion 170 in FIG. 3. In some embodiments, the cut-out portion 174 can couple to the coupling portion 170. In some embodiments, the cut-out portion 174 is a passage wherein the coupling portion 170 protrudes roughly planar to the first major surface 180. The one-way valve 172 can further fluidically couple to the channel 126 of FIG. 3 and contact the coupling portion 170. The one-way valve 172 can be configured to prevent backflow to the reprocessing system because the coupling portion 170 can receive disinfectant from a reprocessing system.

In some embodiments, the cut-out portion 174 can have a cut-out portion area formed from the second housing therein, which is defined by an area of the cut-out portion planar the first major surface 180 of the second housing. The cut-out portion area can be greater than that of the first coupling portion area.

The second housing can also have a second coupling portion 178 that is configured to allow disinfectant to flow out. For example, the second coupling portion 178 can have a passage 176 where disinfectant flows out. The second coupling portion 178 can be configured to couple to a harness adaptor or generally attach to a reprocessing system. The passage 176 can be fluidically coupled to the second side of a filter membrane (not shown) and positioned in the second housing 112.

The second coupling portion 178 can be planar with the first major surface and resides adjacent a portion of the sealing element 150 of the first housing 110 (with the first membrane 152 between). For example, the second coupling portion 178 is planar to the first major surface 180 and within the perimeter of the sealing element 150. In some embodiments, the second coupling portion 178 can be adjacent to a depressed portion 144 of the first major surface 180. The depressed portion 144 can provide extra compression to the filter membrane. This configuration can have the effect of concentrating the flow of disinfectant. The second coupling portion 178 can also be within the perimeter of the depressed portion 144 but raised such that the second coupling portion 178 is planar with the first major surface 180.

Figure 6:
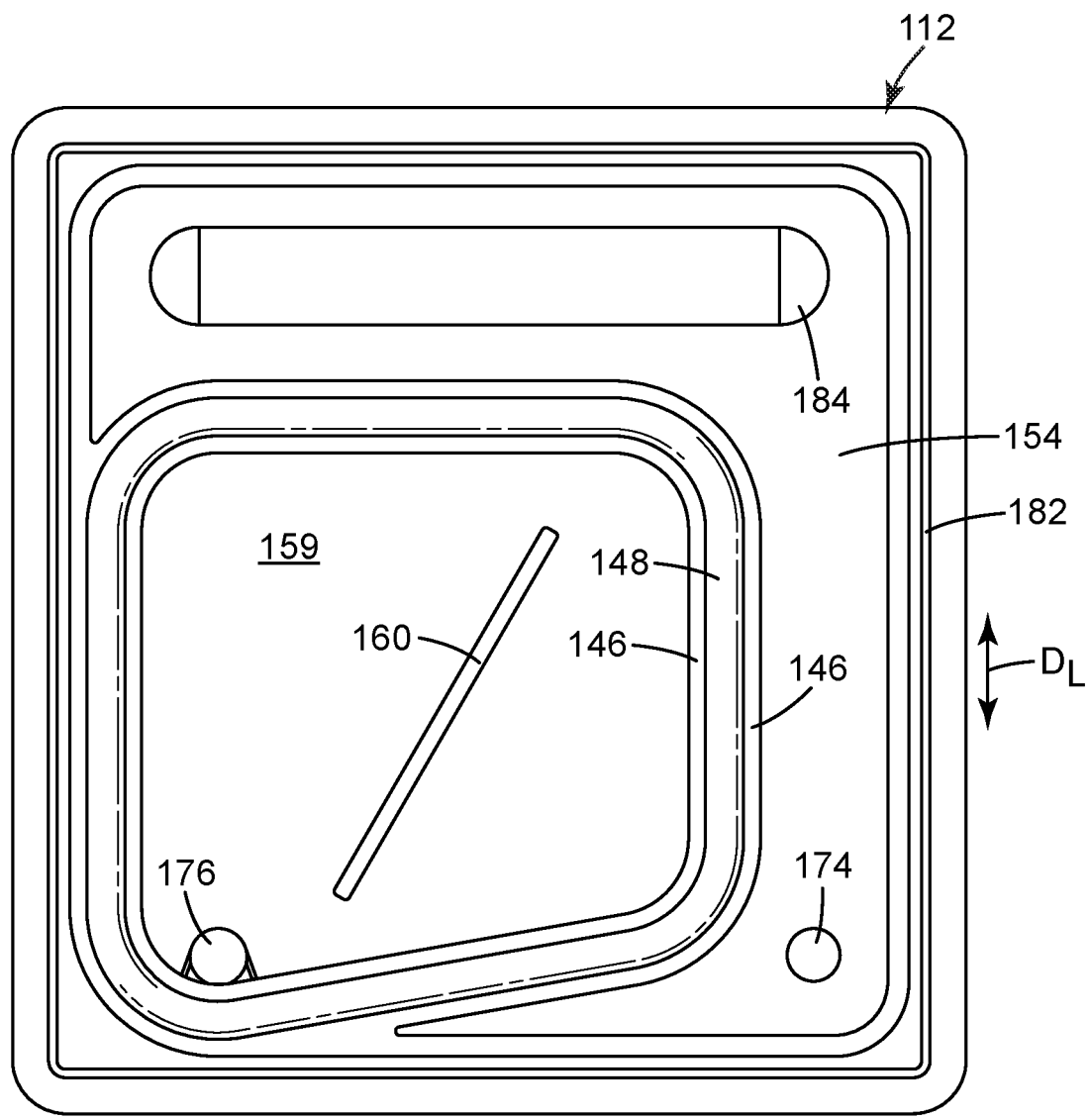
FIG. 6 is a rear perspective view of the second housing of the microbial indicator device of FIGS. 1 and 5.

In FIG. 6, a second major surface 154 and the one or more side portions 182 of the second housing 112 are shown. The second major surface 154 can contact the filter membrane and the second major surface 109 of the first housing 110 as shown in FIG. 3. The second major surface 154 can have one or more raised portions (e.g., raised portion 146, and raised portion 159) and/or depressed portions. For example, a depressed portion 184 can create a cavity sufficient to accommodate the raised portion 166 in FIG. 2 when the second housing 112 is mated with the first housing 110.

In another example, a raised portion 159 can correspond to the depressed portion 144 in FIG. 5. The raised portion 159 is configured to define the boundaries of the second fluidic path. The raised portion 159 can also have a raised diverter 160 which is positioned to correspond to the raised diverter 158 in FIG. 2. For example, the raised diverter 158 of the second major surface 109 of the first housing 110 in FIG. 2 is positioned to align with the raised portion 160 of the second major surface 154 of the second housing 112.

The raised portion 146 can define the boundaries of the sealing element 148. For example, the raised portion 146 is configured to position a portion of the sealing element 148.

The second major surface 154 can also include the cut-out portion 174 that goes through the second housing 112.

As shown in FIG. 6, a disinfectant 190 can originate in the first housing and can flow through the second fluid path. The second fluid path can include the filter membrane and the disinfectant 190 can flow through the filter membrane into a second filter cavity defined by the raised portion 146 and the sealing element 148. The disinfectant 190 can flow out of the passage 176 and into the reprocessing system.

Figure 7:
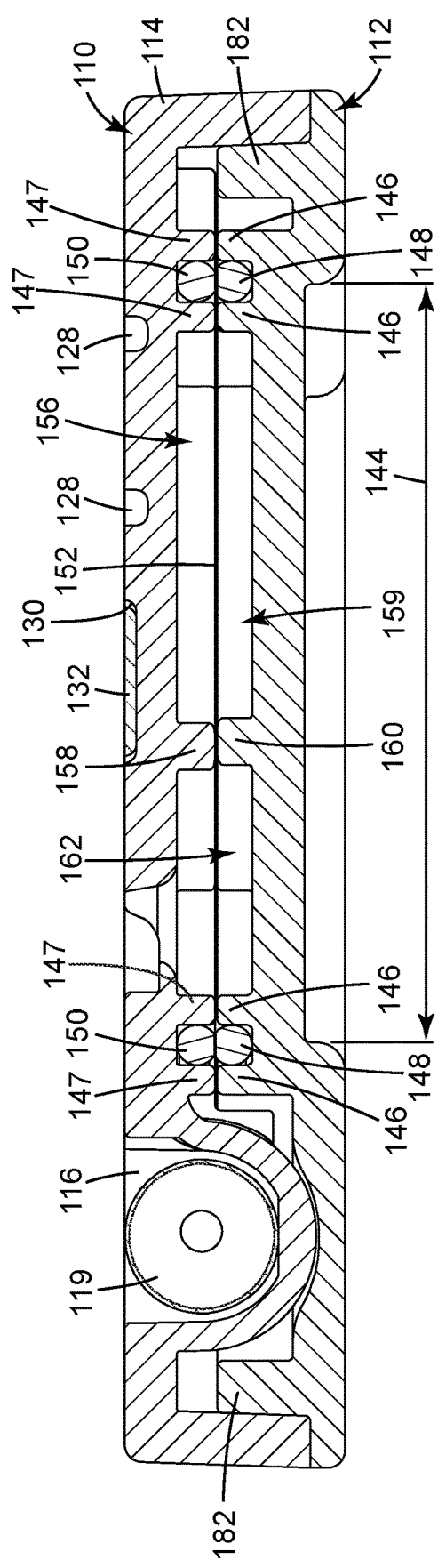
FIG. 7 is a side cross-sectional view of the microbial indicator device of FIG. 1 taken along line 7-7 of FIG. 1, the microbial indicator device is shown in a first state.
Figure 8:
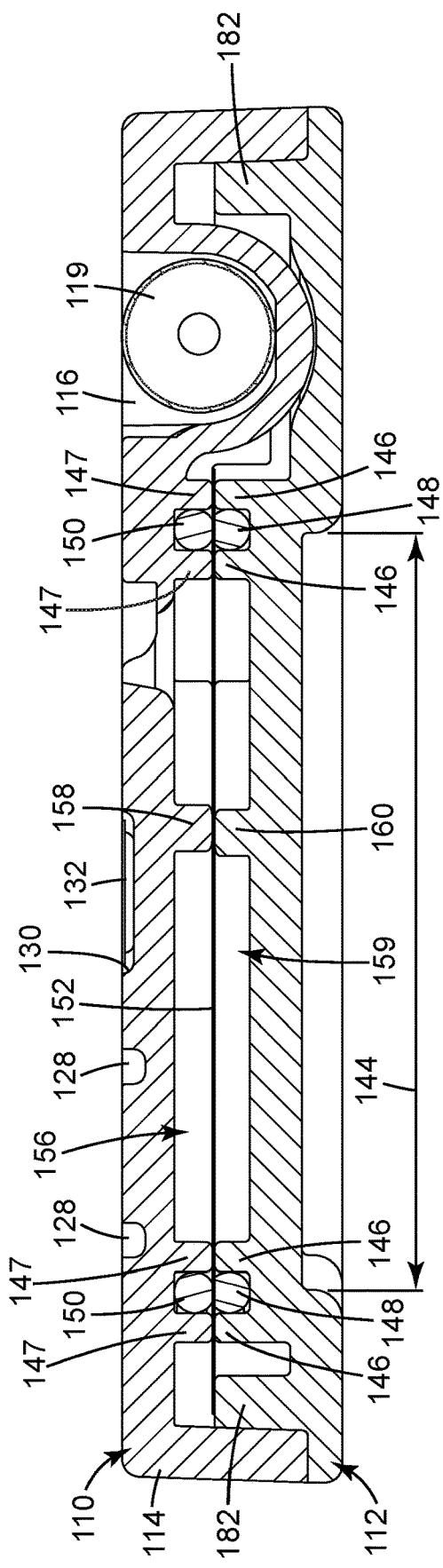
FIG. 8 is a side cross-sectional view of the microbial indicator device of FIG. 1 taken along line 8-8 of FIG. 1, the microbial indicator device is shown in a first state.

FIGS. 7 and 8 show two side cross sectional views of the microbial indicator device 100. The first housing 110 and the second housing 112 can be formed from two separate components. The side portions 114 of the first housing 110 can align slightly offset from the side portions 182 of the second housing 112 such that the side portions 114 mate with the one or more side portions 182 of the second housing 112.

The filter membrane 152 can be sandwiched between the first housing 110 and the second housing 112. A portion of the filter membrane 152 can be contained by the raised portions 146 and 147. To enhance the seal between the housings and the filter membrane 152, one or more sealing elements can be used. If used, the filter membrane 152 surface area is based on the perimeter at least one of the sealing elements, preferably the sealing element 150.

In some embodiments, the filter membrane 152 can be compressed between the sealing element 150 and the sealing element 148. The first side of the filter membrane can be oriented toward the first housing 110 and can define the first filter cavity 156. The second side of the filter membrane can be oriented opposite the first housing 110 and can define the second filter cavity 162. The second filter cavity 162 can be defined by the second major surface of the second housing 112 and optionally the raised portion 159.

In use, a user can perform a method of operating a microbial indicator device. The user could obtain the microbial indicator device as discussed herein. The user could also connect the liquid input to a reprocessing system and preferably with a harness adaptor. The user could then allow the liquid sterilization agent or disinfectant to flow through the second fluidic path of microbial indicator device. For example, the disinfectant could enter through the coupling portion 170 and through the channel 126. The disinfectant could then pass through one or more channels through at least a second cavity 134 and a carrier 136 containing a source of biological activity 137. After passing through the carrier 136, the disinfectant could proceed through the drain passage 138 and proceed into the first filter cavity 156. The disinfectant could pass through the filter membrane 152 into the second filter cavity 162. Since the filter membrane 152 is of a size sufficient to resist passage of sources of biological activity (e.g., vegetative organisms), a portion of the source of biological activity can be retained within the first filter cavity 156. The disinfectant could exit the microbial indicator device 100 through passage 176 of the second coupling portion 178.

To verify an acceptable disinfection process, a liquid 119 such as a nutrient medium can be applied to the source of biological activity 137 to verify disinfection and follow a first fluidic path. For example, a user or reprocessing system can fracture the container 118 containing the liquid 119. The container 118 can be changed from the first state to the second state. The microbial indicator device 100 can be oriented along the longitudinal axis such that the liquid 119 is diverted into the second cavity 134 containing the carrier 136 containing a source of biological activity 137.

The liquid 119 can be passed through a funneling cavity 120 and into a drain passage 124. The liquid 119 can flow along the portion of second major surface 109 interior to raised portion 147 and be bordered by the filter membrane 152, the second major surface 109 and one or more raised portions 147. A diverter 158 can help direct the liquid 119 into the drain passage 138 and to the source of biological activity 137. In some embodiments, residual sources of biological activity may be present on the surface of the filter membrane 152 and prevented from flowing through the second coupling portion of the microbial indicating device 100. A user or a reading apparatus can then determine whether the source of biological activity 137 is biologically active.

Figure 9:
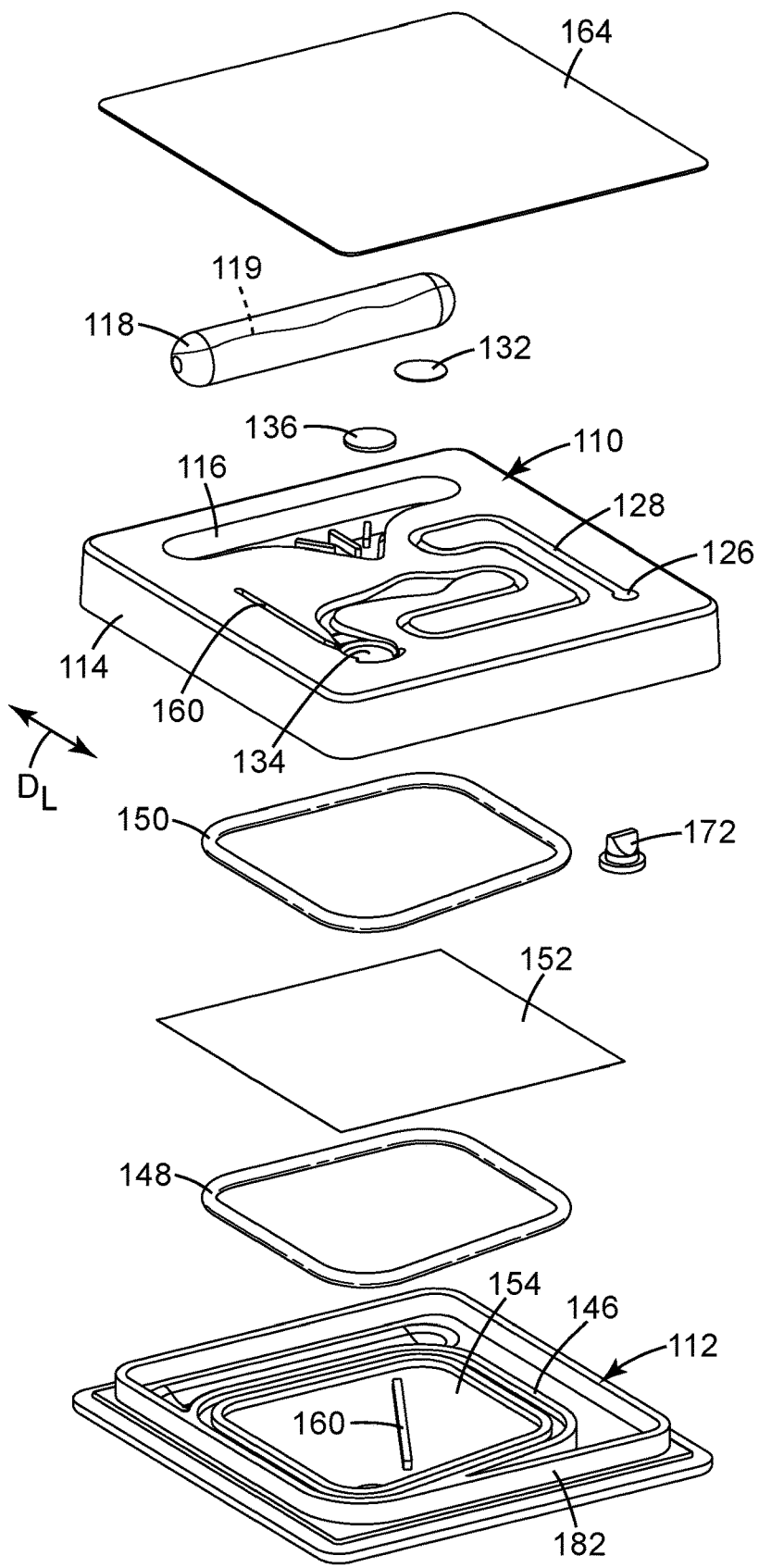
FIG. 9 is an expanded front-side perspective view of the microbial indicator device of FIGS. 1-3

FIG. 9 illustrates an exploded view of the microbial indicator device 100. The microbial indicator device 100 can have a cover 164 adjacent the first major surface of the first housing. The cover 164 can be configured to hermetically seal the one or more channels and can be a laminating film.

Such a cover 164, if employed, can be formed of a material that does not substantially impede a detection process, and/or which is at least partially transmissive to electromagnetic radiation wavelengths of interest. The cover 164 material can also be a material that is not pervious to either the disinfectant from the reprocessing system or liquid 119. In some embodiments, the cover 164 can also contain features for facilitating fluid flow into the second cavity 134, such as capillary channels, hydrophilic microporous fibers or membranes, or the like, or a combination thereof. In addition, in some embodiments, the cover can isolate a signal, or enhance the signal, which can facilitate detection. The cover can include a variety of materials, including, but not limited to, paper, a polymer (e.g., any of the polymers listed above with respect to the housing 110), an adhesive (e.g., acrylate, natural or synthetic rubber, silicone, silicone polyurea, isocyanate, epoxy, or combinations thereof), a woven cloth, a nonwoven cloth, a microporous material (e.g., a microporous polymeric material), a glass, a porcelain, a ceramic, a gel-forming material (e.g., guar gum), or combinations thereof.

FIG. 10 illustrates a cartridge system 1000 with a microbial indicator device 1002 and a harness adaptor 1001. The microbial indicator device 1002 can correspond to the microbial indicator device 100 of FIGS. 1-9 and have similarly numbered components. Microbial indicator device 1002 can further include a locking tab 1097 to interface with the harness adaptor 1001. The microbial indicator device 1002 can have a first coupling portion 1070 and an second coupling portion 1078 for mating with the harness adaptor 1001.

The harness adaptor 1001 can have an first conduit tube 1099 configured to couple the first coupling portion 1070 of the microbial indicator device 1002 and the liquid input from a reprocessing system and a second conduit tube 1098. Additionally, the first conduit tube 1099 has a shape that corresponds to a conduit of an endoscope.

The second conduit tube 1098 can be configured to couple the second coupling portion 1078 of the microbial indicator device and the liquid output from a reprocessing system such as an AER.

The harness adaptor 1001 can also include an outer cover member for holding both of the other ends of the first and second conduit tubes 1099, 1098, such that the steriliant can enter into the microbial indicator device 1002. The microbial indicator device 1002 can be inserted into harness adaptor 1001 by applying downward force in the longitudinal direction $D_L$.

In use, a user would first connect the microbial indicator device 1002 directly to the reprocessing system using a harness adaptor 1001. The system 1000 would be placed in the basin of the reprocessing system that also holds the scope to be reprocessed and would be fully immersed in disinfectant during the cycle. After completion of the cycle, the user would disconnect the system 1000 from the reprocessing system and first visualize the colorimetric response of the chemical indicator to establish if the minimum effective concentration (MEC) of disinfectant was achieved. If the source of biological activity 137 was based on detecting a response from the growth of viable organisms coated directly in the chamber of the device or on a suitable substrate placed in the chamber of the device, the user would next activate the source of biological activity 137 by breaking a frangible vial containing growth media allowing media to enter the chamber holding the indicator. The device would then be placed in an incubator also capable of reading the response from the source of biological activity 137. Depending on the effectiveness of the reprocessing system's disinfection cycle, a response would then be detected at a determined time point to establish if the cycle had passed or failed.

Figure 12A:
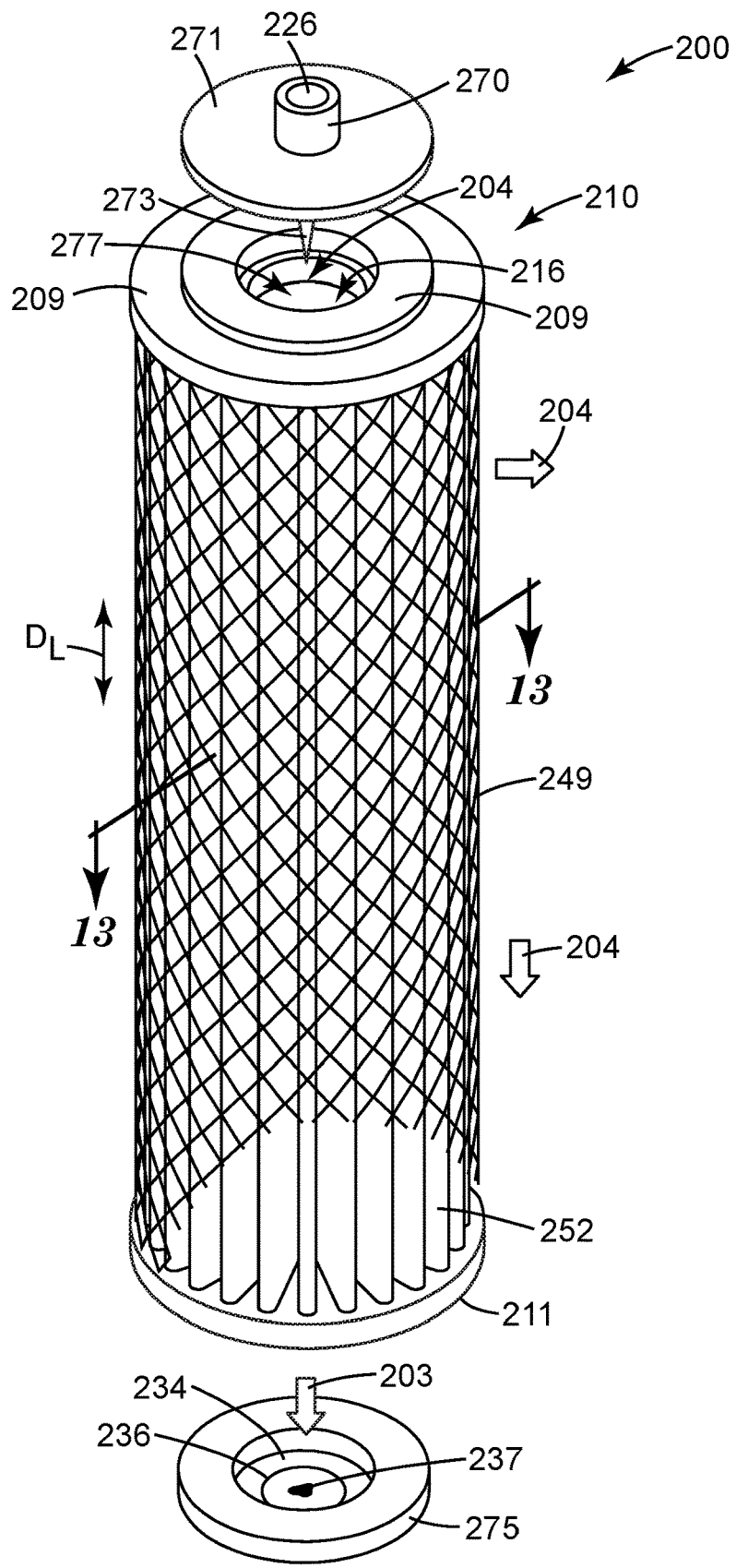
FIG. 12A is an expanded front-side perspective view of another embodiment of a microbial indicator device.
Figure 12B:
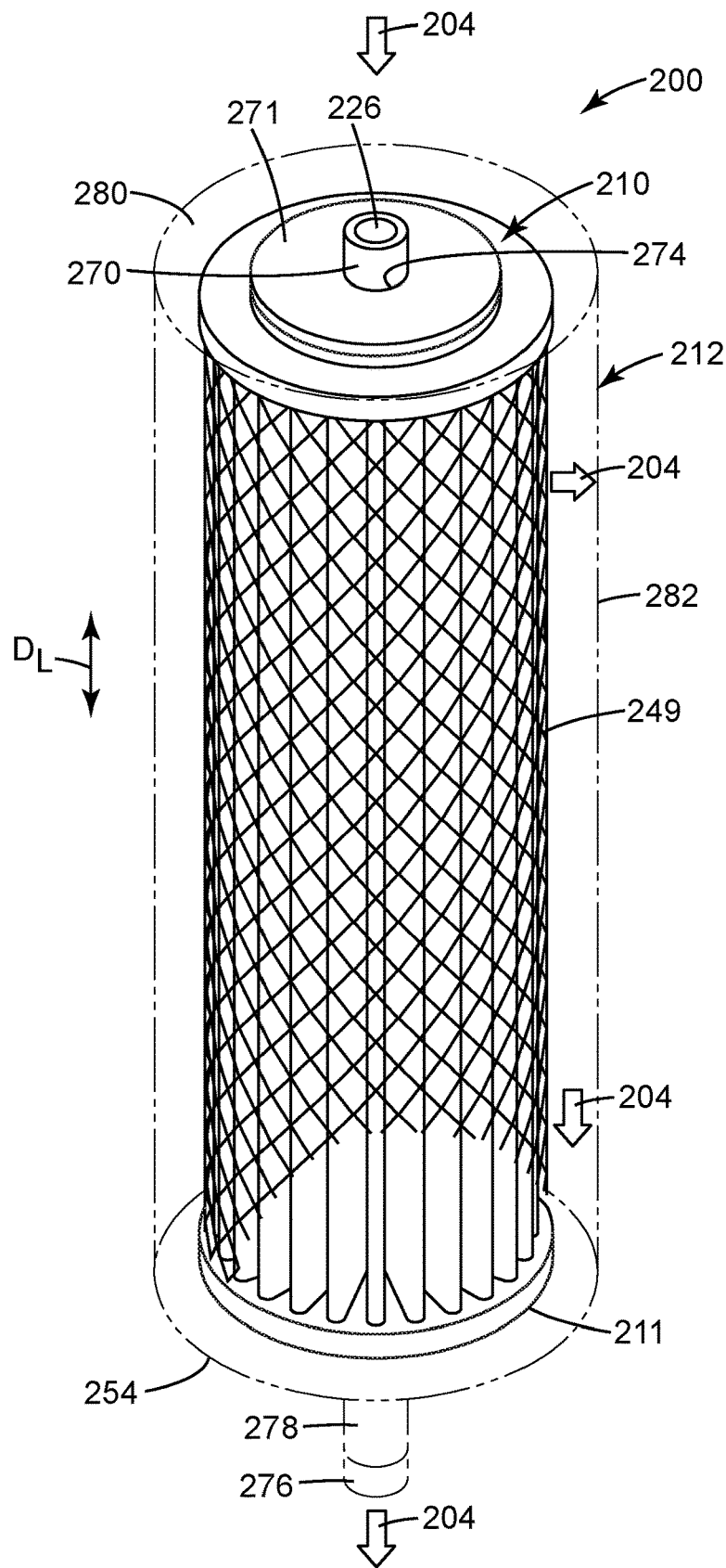
FIG. 12B is an expanded front-side perspective view of another embodiment of a microbial indicator device shown with a second housing.

FIGS. 12A-B illustrates another embodiment of a microbial indicator device 200 the present disclosure. The microbial indicator device 200 can be similar to the microbial indicator device 100 of FIGS. 1-9 in that both have at least a cavity, source of biological activity, and a filter membrane and both have similarly numbered components. The microbial indicator device 200 can be cylindrical. The cylindrical shape can be advantageous because the total surface area of a filter membrane 252 is greater than a two dimensional structure. The cylindrical shape may also have manufacturing advantages. The microbial indicator device 200 can have a first housing 210 and a second housing 212.

As shown, the first housing 210 can have a filter membrane 252 attached or secured via a retention mechanism 249 (such as a mesh or other mechanical or adhesive attachment). The first housing 210 may also have a cover 271 as a separate or integral component to the first housing. The cover 271 can form a hermetic seal with the major surface 209. An optional sealing element 250 can also be present. The cover can also have an optional breaking mechanism 273 such as a metallic or polymeric spike to aid in breaking the container (not shown) and changing the container (not shown) from a first state to a second state. The cover 271 can have a coupling portion 270 that is configured to couple with an inlet from a reprocessing system or adaptor. A second fluidic path 204 can be established through an channel 226 which can allow a disinfectant to flow into the microbial indicator device 200.

The second fluidic path 204 can also be established through a channel 277. The channel 277 can extend through the first housing 210 all the way to the plate 275. The channel 277 can preferably be pervious to a disinfectant such that the disinfectant can flow through to the filter membrane 252. The channel 277 can be modified to have one or more passages 269 to further promote the flow of disinfectant to the filter membrane 252. The channel 277 can further form a cavity 216. The cavity 216 can house the container 218 which is filled with a liquid 219.

The plate 275 can be configured to contain the source of biological activity 237. For example, the source of biological activity 237 could be deposited directly onto the plate 275. The source of biological activity 237 is shown as being present on a carrier 236 and being further housed in cavity 234. The plate 275 is shown as separate from the first housing 210. It can be preferable to have the plate 275 integral with the first housing in certain situations. For example, if the plate 275 is integral, then the cavity 216 is likely to maintain the seal. In some embodiments, the plate 275 can be removable such that the source of biological activity 237 can be replaced. The plate 275 can be configured to form a hermetic seal with the channel 277 such that pressurized liquid is diverted from the channel 277 through the filter membrane 252. The filter membrane 252 can prevent the source of biological indicator 237 from transporting into a reprocessing system while providing a lower resistance of flow.

Figure 13:
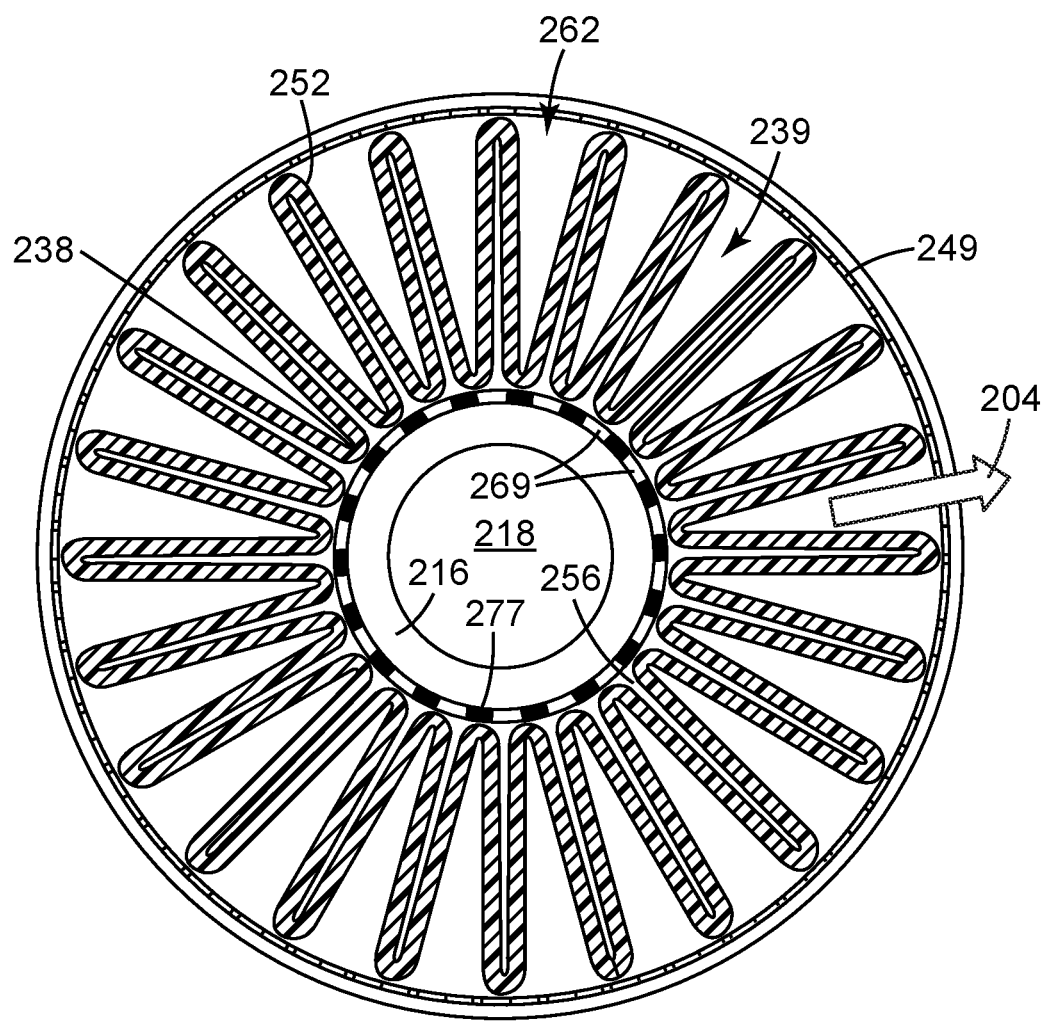
FIG. 13 is a top cross-sectional view of the microbial indicator device of FIG. 12A taken along line 13-13 of FIG. 12A.

FIG. 13 shows how the container 218 is positioned in the cavity 216 formed by the channel 277. The filter membrane 252 can be folded to maximize the surface area relative to a two-dimensional configuration. A filter cavity 256 can form in the region between the channel 277 and the filter membrane 252 while the filter cavity 262 can form from a second side of the filter membrane 252 (which can also be referred to as a liquid outlet 239). The second fluidic path 204 can be established from the filter cavity 256 to the filter cavity 262.

Returning to FIG. 12, optionally, microbial indicator device 200 can have a second housing 212. The second housing can divert disinfectant from the first housing 210 to a second coupling portion 276. Thus, the second fluidic path 204 is established from liquid outlet 239 through the second coupling portion 276. The second housing 212 can further have a raised portion 278 for coupling to a reprocessing system or adaptor. The second housing 210 can further have a side portion 282 and major surface 280 and major surface 254. The major surface can have a cut-out portion 274 that is configured to abut the coupling portion 270.

In some embodiments, at least a portion of the second housing 212 can form a seal with the first housing 210. For example, major surface 280/side portion 282 can form a seal with any portion of major surface 209 or major surface 254/side portion 282 can form a seal with any portion of major surface 211.

The first fluidic path 203 can be established within the channel 277. For example, the container 218 can be changed from the first state to a second state by inverting or shaking the container along the longitudinal axis such that the container 218 contacts the breaking mechanism 273. The liquid 219 can flow with gravity and contact the source of biological activity 237. To aid in a visual verification of disinfection, at least a portion of the plate 275 can be transparent meaning that a luminescence or color change is discernable with the human eye or instrumentation.

Figure 14A:
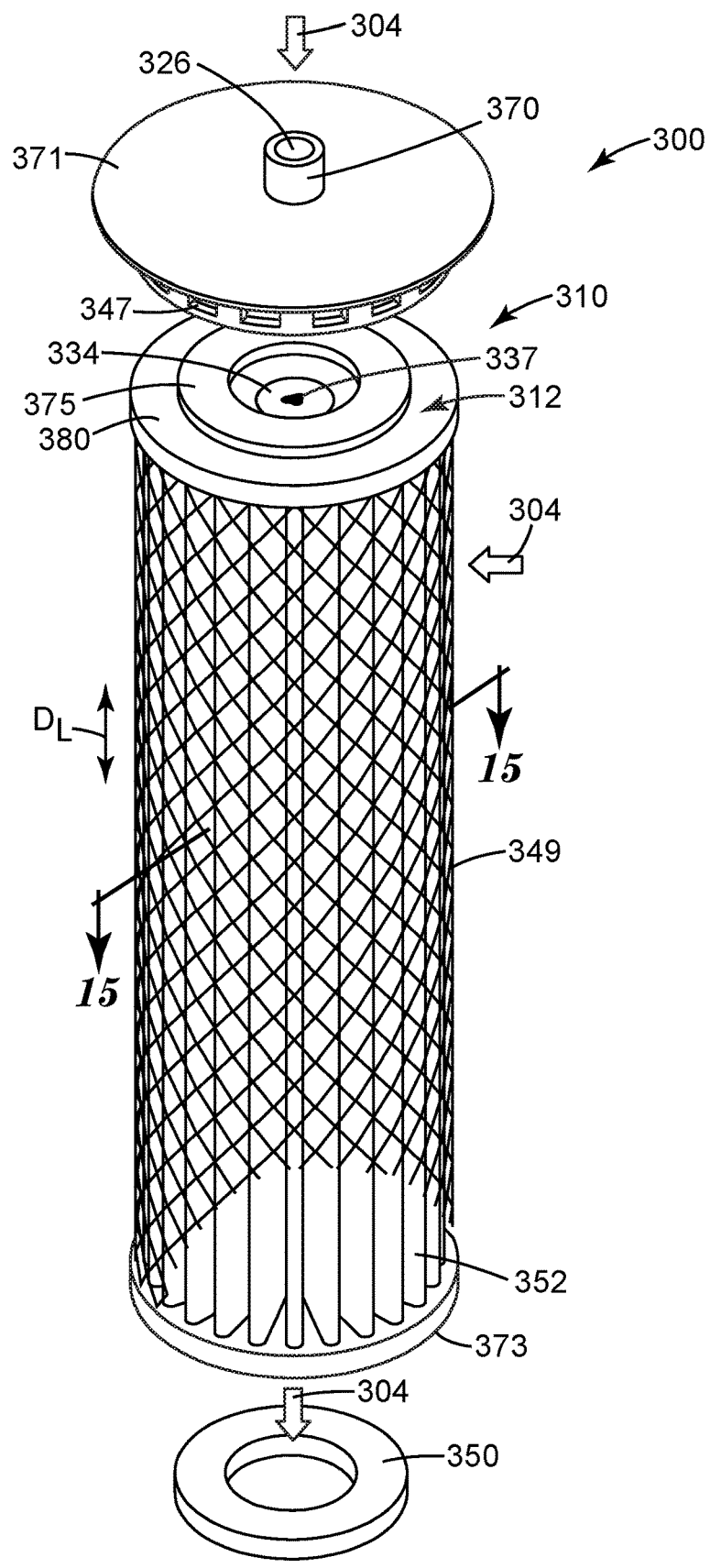
FIG. 14A is an expanded front-side perspective view of a yet another microbial indicator device.
Figure 14B:
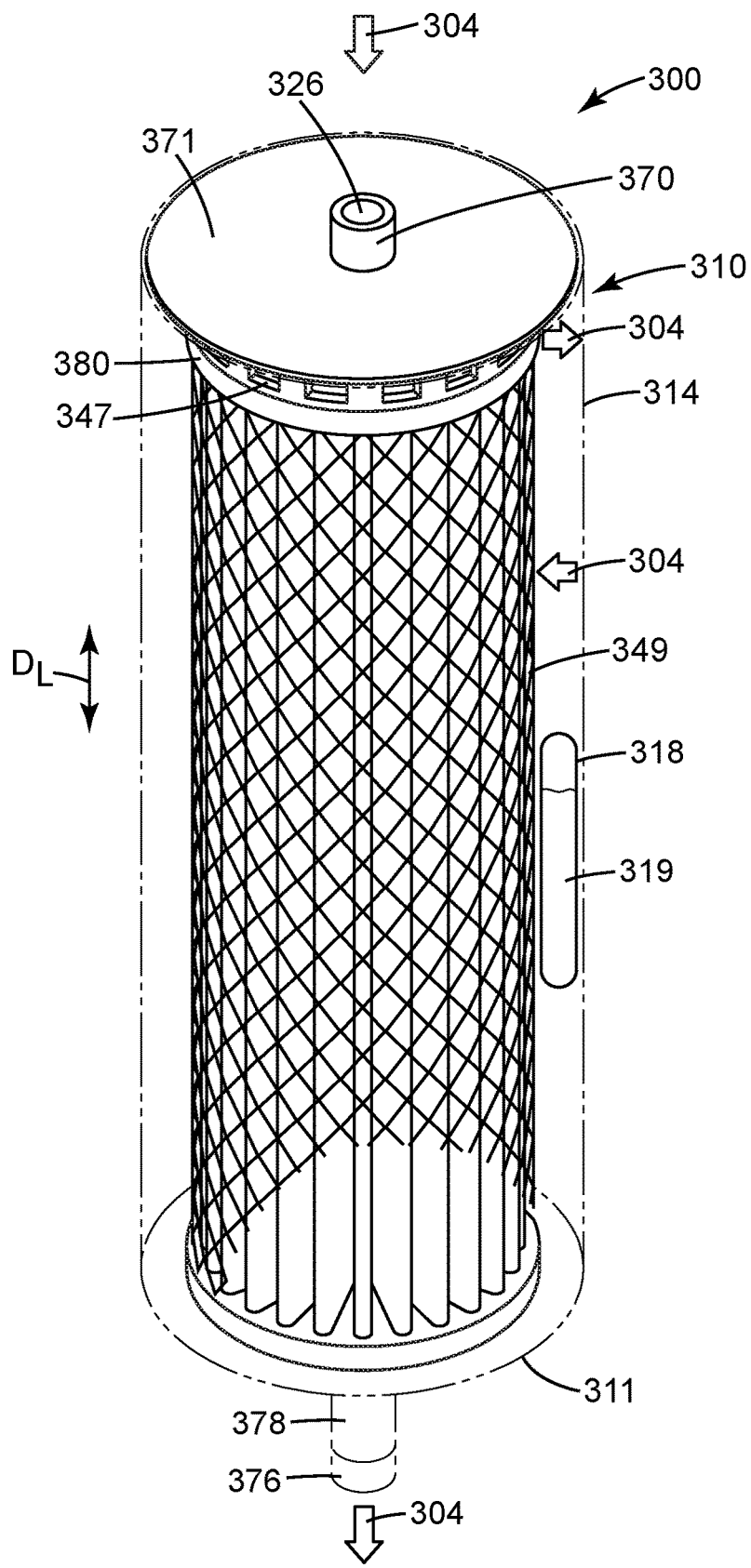
FIG. 14B is an expanded front-side perspective view of another embodiment of a microbial indicator device shown with a second housing.

In FIGS. 14A-B, another embodiment of a microbial indicator device 300 is shown. The microbial indicator device 300 is similar to the microbial indicator device 200 in FIGS. 12-13 except that the direction of flow of the second fluidic path is reversed and a first housing 310 forms an outer component of the microbial indicator device 300.

In FIG. 14B, the first housing 310 can have a side portion 314 with a portion facing the cavity 316. The cavity 316 can house a container 318 having a liquid 319. The first housing 310 can be sufficiently flexible such that the container 318 can be broken by manually flexing the container 318.

The first fluidic path can be established from the container 318 to the source of biological activity 337 in FIG. 14A by inverting the container such that the liquid 319 is carried with gravity toward the source of biological activity 337 in FIG. 14A along the longitudinal axis.

The first housing 310 can also have a cover 371 one or more spacing components 347 and a coupling portion 270 with a channel 326 formed therein. Although FIG. 14B shows that cover 371 and side 314 are separate for illustrative purposes, the cover 371 forms a liquid seal with the side 314 of the first housing 310. The spacing component 347 which can raise the cover 371 to create a fluidic channel over the plate 375 in FIG. 14A.

In FIG. 14A, the plate 375 can include a cavity 334 that contains a carrier 336 and a source of biological activity 337. The plate 375 can be secured or molded to the cover 371. In some embodiments, the plate 375, cover 371, side portion 314 are molded as a single piece of the housing 310. Parts of the first housing 310 (such as the cover 371) can be transparent to allow visual observation of a color change in the source of biological activity 337.

Figure 15:
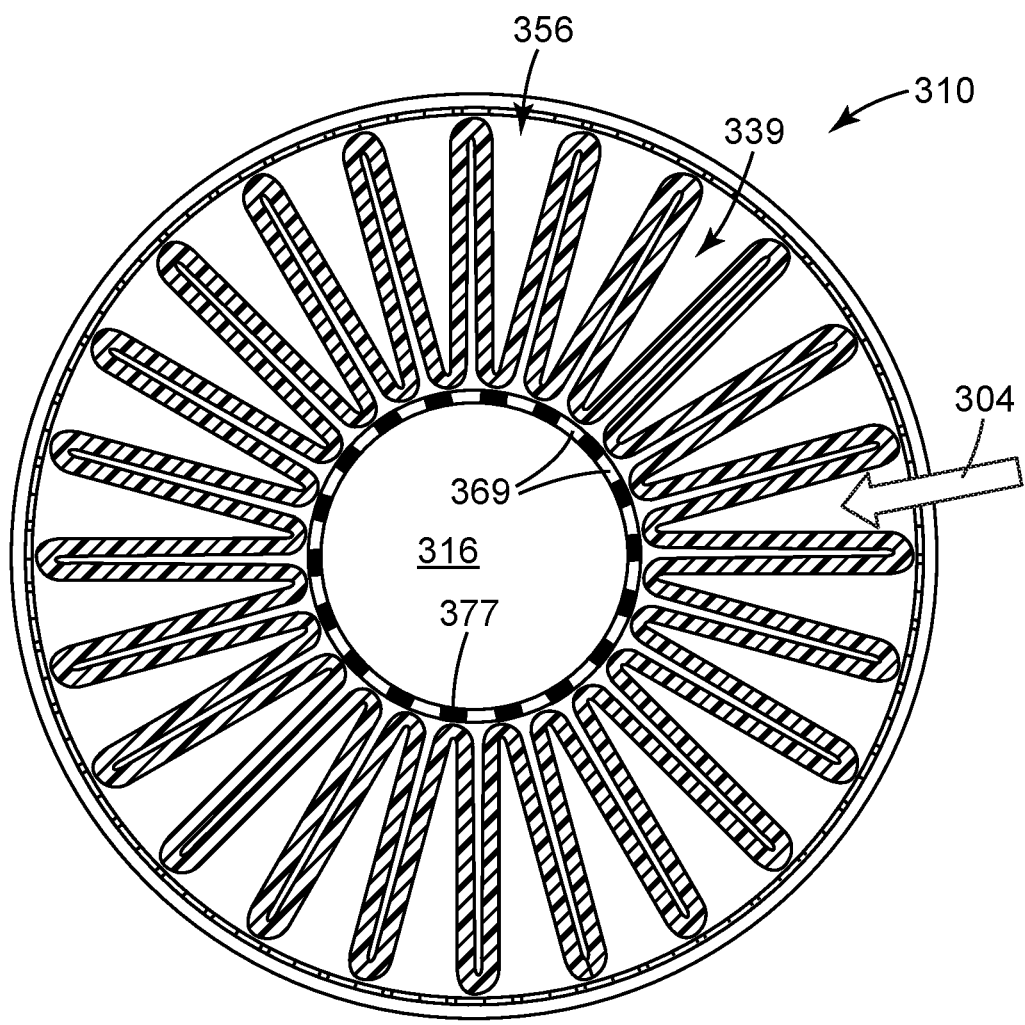
FIG. 15 is a top cross-sectional view of the microbial indicator device of FIG. 14A taken along line 15-15 of FIG. 14A.

The microbial indicator device 300 can also have a second housing 312. In some embodiments, the second housing 312 is configured to hold the filter membrane 352. The filter membrane 352 can be additionally secured to the second housing 312 via a retention mechanism 349. The second housing 312 can have a channel 377 as shown in FIG. 15.

The channel 377 can also have one or more passages and extend through a cover with a hole formed therein 373. The cover 373 can be formed with the second housing 312 and be configured to form a hermetic seal with the first housing 314. For example, the cover 373 can use a sealing element 350 to form a hermetic seal with the bottom face of the first housing 311. The bottom face 311 can include the second coupling portion 376 as well as a raised portion 378 to couple with a reprocessing system or adaptor.

The first housing 310 can form a seal with the second housing 312 such that disinfectant is transported through the filter membrane 352 without the presence of leaks. Thus, cover 373 of the second housing 312 can form a seal with a side portion 314 of the first housing 310 but an edge of major surface 380 does not need to form a seal with the first housing 310.

The second fluidic path 304 can be established by the first coupling portion 370 through the second coupling portion 376. The second fluidic path 304 can pass thru the gaps defined by the spacing component 347 along a side portion 314 of the first housing 310. Pressure can direct a disinfectant through the filter membrane 352 where the disinfectant passes thru the first filter cavity 356 to the second filter cavity 362 (contacting the second side of the filter membrane 339) and into the channel 377 as shown in FIG. 15. The second fluidic path 304 can then proceed through the second coupling portion 376.

Figure 16:
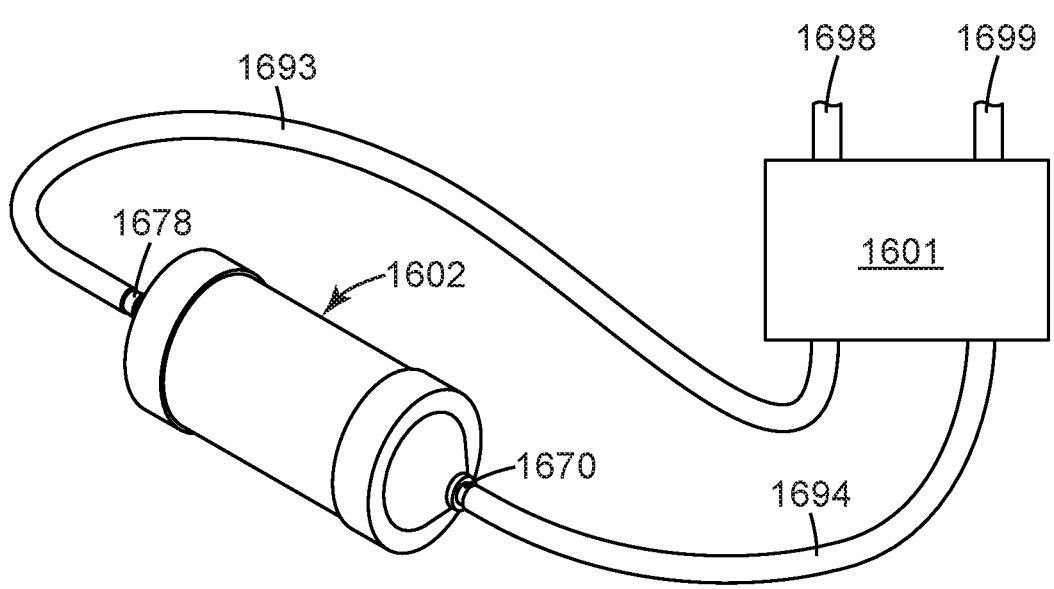
FIG. 16 is a front perspective view of a microbial indicator device and an adaptor.

FIG. 16 shows a system 1600 that includes an adaptor 1601 for a microbial indicator device 1602. The microbial indicator device 1602 can correspond to the microbial indicator device 200 of FIGS. 12-13 or the microbial indicator device 300 of FIGS. 14-15 and have similarly numbered components. The adaptor 1601 can be similar to the adaptor 1001 in FIG. 10 and have similarly numbered components.

The adaptor 1601 can fluidically couple to a conduit tube 1699 and a conduit tube 1698 from a reprocessing system. Additionally, the first conduit tube 1699 has a shape that corresponds to a conduit of an endoscope. The second conduit tube 1098 can be configured to couple the second coupling portion 1078 of the microbial indicator device and the liquid output from a reprocessing system.

The microbial indicator device 1602 can have a first coupling portion 1670 and an outlet 1678 for mating with the adaptor 1001. Tubes 1694, 1093 can be configured to couple with both the adaptor 1601 and the microbial indicator device 1602.

LIST OF ILLUSTRATIVE EMBODIMENTS

Embodiment 1

A microbial indicator device for a liquid disinfecting step, comprising:
  a first housing comprising:
    a first cavity;
    a source of biological activity, wherein the source of biological activity is fluidically coupled to the first cavity via a portion of a first fluidic path;
  a first coupling portion having a first channel extending longitudinally therethrough that defines a portion of a second fluidic path, wherein the first coupling portion is fluidically coupled the source of biologically activity via the second fluidic path;
  a filter membrane positioned in the second fluidic path, wherein the filter membrane has a first side and a second side, wherein the second fluidic path is established between the first coupling portion and the second side,
  wherein the filter membrane has effective porosity sufficient to retain at least a portion of the source of biological activity on the first side.

Embodiment 1a

The microbial indicator device of any of the preceding embodiments, wherein when a disinfectant is received at the first coupling portion at a first pressure at 25 degrees C., and the disinfectant exits the second side at a second pressure at 25 degrees C., the second pressure is at least 90 percent of the first pressure.

Embodiment 1b

The microbial indicator device of any of the preceding embodiments, wherein the first housing has a second channel formed therein that defines a portion of the second fluidic path.

Embodiment 1c

The microbial indicator device of any of the preceding embodiments, wherein the second channel formed from the first housing follows a tortuous path having a first resistance to flow of a disinfectant.

Embodiment 1d

The microbial indicator device of any of the preceding embodiments, wherein the filter membrane has a second resistance to a flow of a disinfectant.

Embodiment 1e

The microbial indicator device of any of the preceding embodiments, wherein the second fluid resistance is no greater than the first fluid resistance.

Embodiment 1f

The microbial indicator device of any of the preceding embodiments, wherein the first coupling portion is adapted to receive a liquid that, when combined with the source of biological activity, allows the source of biological activity to produce a visual indication of an adequate disinfection process, wherein the liquid follows the first fluidic path.

Embodiment 1g

The microbial indicator device of any of the preceding embodiments, wherein the second fluidic path is at least partially established in the first housing.

Embodiment 1h

The microbial indicator device of any of the preceding embodiments, further comprising a second cavity positioned in the first housing and configured to house a source of biological activity, wherein the second cavity is fluidically coupled to the first cavity via a portion of the first fluidic path.

Embodiment 1i

The microbial indicator device of any of the preceding embodiments, wherein the second cavity is positioned in the second fluidic path.

Embodiment 1j

The microbial indicator device of any of the preceding embodiments, wherein the second fluidic path is designed in a tortuous path to mimic the geometry of an endoscope.

Embodiment 1k

The microbial indicator device of any of the preceding embodiments, wherein the filter membrane is positioned adjacent the second channel.

Embodiment 1l

The microbial indicator device of any of the preceding embodiments, wherein the filter membrane is positioned adjacent the source of biological activity.

Embodiment 1m

The microbial indicator device of any of the preceding embodiments, further comprising a container containing a liquid and being dimensioned to be positioned in the first cavity, at least a portion of the container being frangible, the container having a first state in which the container is intact and the liquid is not in fluid communication with an interior of the first cavity and a second state in which the container is fractured and the liquid is in fluid communication with the first cavity.

Embodiment 2

The microbial indicator device of any of the preceding embodiments, wherein the filter membrane has a filter membrane surface area and the first coupling portion has an inlet area partially defined by a cross-section of the first channel, wherein the ratio of the filter membrane surface area to inlet area is at least 2:1.

Embodiment 2a

The microbial indicator device of any of the preceding embodiments, wherein the resistance to flow of the filter membrane is no greater than 55 $mm^{-3}$ at 25 degrees C.

Embodiment 3

The microbial indicator device of any of the preceding embodiments, wherein the ratio of the filter membrane surface area to inlet area is at least 10:1.

Embodiment 4

The microbial indicator device of any of the preceding embodiments, wherein the ratio of the filter membrane surface area to inlet area is at least 100:1.

Embodiment 5

The microbial indicator device of any of the preceding embodiments, wherein the second channel has a cross-sectional area, wherein the ratio of the filter membrane surface area to cross-sectional area is at least 100:1.

Embodiment 6

The microbial indicator device of any of the preceding embodiments, further comprising:
a chemical indicator that indicates whether a process results in sufficient disinfection.

Embodiment 6a

The microbial indicator device of any of the preceding embodiments, further comprising:
a third cavity positioned in the second fluidic path.

Embodiment 6b

The microbial indicator device of any of the preceding embodiments, wherein the third cavity is positioned in the first housing and configured to house the chemical indicator

Embodiment 6c

The microbial indicator device of any of the preceding embodiments, wherein the third cavity is fluidically coupled to the first coupling portion via the second fluidic path.

Embodiment 7

The microbial indicator device of any of the preceding embodiments, further comprising a vent.

Embodiment 8

The microbial indicator device of any of the preceding embodiments, wherein a third channel is formed from a portion of the first housing, wherein the vent is coupled to the second cavity via the third channel.

Embodiment 9

The microbial indicator device of any of the preceding embodiments, wherein the vent has an opening having an opening area and the second cavity has a second cavity cross-sectional area, wherein the opening area is no greater than the second cavity cross-sectional area.

Embodiment 10

The microbial indicator device of any of the preceding embodiments, wherein the vent has an opening having an opening area and the second cavity has a second cavity cross-sectional area, wherein the opening area is no greater than the second cavity cross-sectional area.

Embodiment 11

The microbial indicator device of any of the preceding embodiments, further comprising a cover.

Embodiment 11a

The microbial indicator device of any of the preceding embodiments, wherein the cover has the first coupling portion formed therein.

Embodiment 11b

The microbial indicator device of any of the preceding embodiments, wherein the microbial indicator device is cylindrical.

Embodiment 11c

The microbial indicator device of any of the preceding embodiments, further comprising a retention mechanism.

Embodiment 11d

The microbial indicator device of embodiment 11c, wherein the retention mechanism is disposed on at least a portion of the filter membrane.

Embodiment 11e

The microbial indicator device of any of the preceding embodiments, wherein the filter membrane is three-dimensional.

Embodiment 11f

The microbial indicator device of any of the preceding embodiments, wherein the first housing has a fourth channel formed therein.

Embodiment 11g

The microbial indicator device of any of the preceding embodiments, wherein the first housing comprises a plate.

Embodiment 11h

The microbial indicator device of embodiment 11g, wherein the fourth channel extends longitudinally from the first coupling portion to the plate.

Embodiment 11i

The microbial indicator device of any of the preceding embodiments, wherein the fourth channel comprises one or more passages.

Embodiment 11j

The microbial indicator device of any of the preceding embodiments, wherein the fourth channel is adjacent to the filter membrane.

Embodiment 11k

The microbial indicator device of any of the preceding embodiments, wherein the fourth channel defines the first cavity.

Embodiment 11l

The microbial indicator device of any of the preceding embodiments, wherein the source of biological activity is adjacent to the plate.

Embodiment 11m

The microbial indicator device of any of the preceding embodiments, wherein the second cavity is formed in the plate.

Embodiment 11n

The microbial indicator device of any of the preceding embodiments, wherein the plate seals the fourth channel.

Embodiment 11o

The microbial indicator device of any of the preceding embodiments, wherein the cover seals the fourth channel.

Embodiment 11p

The microbial indicator device of any of the preceding embodiments, wherein the cover further comprises a spacing element.

Embodiment 11q

The microbial indicator device of any of the preceding embodiments, wherein the cover contacts at least a portion of the first housing.

Embodiment 11r

The microbial indicator device of any of the preceding embodiments, wherein the cover is adjacent to the plate.

Embodiment 12

The microbial indicator device of any of the preceding embodiments, further comprising a second housing.

Embodiment 13

The microbial indicator device of any of the preceding embodiments, wherein the first coupling is fluidically coupled to a second coupling portion via the second fluidic path, wherein the second coupling portion forms a fifth channel extending longitudinally therewith, wherein the second coupling portion is positioned in the second housing.

Embodiment 14

The microbial indicator device of any of the preceding embodiments, wherein the second housing comprises at least a first major surface and a second major surface.

Embodiment 14a

The microbial indicator device of any of the preceding embodiments, wherein the first fluidic path exists in the first major surface.

Embodiment 15

The microbial indicator device of any of the preceding embodiments, wherein the first major surface of the second housing comprises a depressed portion which defines a raised portion on the second major surface of the second housing.

Embodiment 16

The microbial indicator device of any of the preceding embodiments, wherein the raised portion on the second major surface of the second housing is configured to position a portion of a second sealing element.

Embodiment 17

The microbial indicator device of any of the preceding embodiments, wherein the raised portion further comprises a first raised diverter.

Embodiment 18

The microbial indicator device of any of the preceding embodiments, wherein the second coupling portion is planar to the first major surface and is adjacent a portion of the second sealing element.

Embodiment 19

The microbial indicator device of any of the preceding embodiments, wherein the second coupling portion is planar to the first major surface and is bordered within a perimeter of the second sealing element.

Embodiment 20

The microbial indicator device of any of the preceding embodiments, wherein the second housing comprises one or more side portions.

Embodiment 21

The microbial indicator device of any of the preceding embodiments, wherein the first housing comprises one or more side portions.

Embodiment 22

The microbial indicator device of any of the preceding embodiments, wherein the one or more side portions of the first housing are configured to mate with the one or more side portions of the second housing.

Embodiment 23

The microbial indicator device of any of the preceding embodiments, the first housing comprises at least a first major surface and a second major surface.

Embodiment 23a

The microbial indicator device of any of the preceding embodiments, wherein the second major surface of the first housing comprises a second raised diverter positioned to align with the first raised diverter.

Embodiment 24

The microbial indicator device of any of the preceding embodiments, wherein the second major surface of the first housing comprises a raised portion configured to position a first sealing element.

Embodiment 25

The microbial indicator device of any of the preceding embodiments, wherein the raised portion of the second major surface of the first housing is positioned to align with the raised portion of the second major surface of the second housing.

Embodiment 26

The microbial indicator device of any of the preceding embodiments, wherein the raised portion of the second major surface of the first housing is trapezoidal.

Embodiment 27

The microbial indicator device of any of the preceding embodiments, further comprising a funneling cavity positioned adjacent to the first cavity and positioned within a portion of the first fluidic path, wherein the funneling cavity is configured to direct the liquid when the container is in the second state towards the second cavity.

Embodiment 28

The microbial indicator device of any of the preceding embodiments, wherein the first housing further comprises a first drain passage formed from the first housing extending between the first major surface and the second major surface.

Embodiment 29

The microbial indicator device of any of the preceding embodiments, wherein the first drain passage is fluidically coupled with the second cavity and the first cavity.

Embodiment 30

The microbial indicator device of any of the preceding embodiments, wherein the filter membrane is sandwiched between the first housing and the second housing.

Embodiment 31

The microbial indicator device of any of the preceding embodiments, wherein the filter membrane is sandwiched between the first sealing element and the second sealing element.

Embodiment 31a

The microbial indicator device of any of the preceding embodiments, wherein the filter membrane is compressed between the first sealing element and the second sealing element.

Embodiment 31b

The microbial indicator device of any of the preceding embodiments, wherein the filter membrane surface area is defined by the raised portion of the second major surface of the first housing.

Embodiment 31c

The microbial indicator device of any of the preceding embodiments, wherein the filter membrane surface area is defined by the first sealing element.

Embodiment 32

The microbial indicator device of any of the preceding embodiments, wherein the first housing mates with the second housing.

Embodiment 32a

The microbial indicator device of any of the preceding embodiments, wherein at least a portion of the cover of the first housing mates with at least a portion of a side of the second housing, wherein a fluidic seal is formed.

Embodiment 32b

The microbial indicator device of any of the preceding embodiments, wherein the second side of the filter membrane is fluidically coupled to the second coupling portion via the second fluidic path.

Embodiment 32c

The microbial indicator device of any of the preceding embodiments, wherein a portion of an inner surface of the side of the second housing is fluidically coupled to the second side of the filter membrane.

Embodiment 32d

The microbial indicator device of any of the preceding embodiments, wherein the second housing forms a sixth channel extending between the first plate and the second plate.

Embodiment 32e

The microbial indicator device of any of the preceding embodiments, wherein the sixth channel is coupled to a first plate and a second plate.

Embodiment 32f

The microbial indicator device of any of the preceding embodiments, wherein the first plate is solid and fluidically seals the sixth channel.

Embodiment 32g

The microbial indicator device of any of the preceding embodiments, wherein the second plate has a cut-out portion formed therein.

Embodiment 32h

The microbial indicator device of any of the preceding embodiments, wherein the filter membrane contacts a portion of the sixth channel.

Embodiment 32i

The microbial indicator device of any of the preceding embodiments, wherein the second housing comprises a retention mechanism.

Embodiment 33

The microbial indicator device of any of the preceding embodiments, wherein the filter membrane forms a first filter cavity between the first side of the filter membrane and the second major surface of the first housing.

Embodiment 34

The microbial indicator device of any of the preceding embodiments, wherein the first filter cavity is further defined by the raised portion of the second major surface of the first housing.

Embodiment 35

The microbial indicator device of any of the preceding embodiments, wherein the filter membrane forms a second filter cavity between the second side of the filter membrane and the second major surface of the second housing.

Embodiment 36

The microbial indicator device of any of the preceding embodiments, wherein the second filter cavity is further defined by the raised portion of the second major surface of the second housing.

Embodiment 37

The microbial indicator device of any of the preceding embodiments, wherein the first drain passage is fluidically coupled with the funneling cavity and the first filter cavity.

Embodiment 38

The microbial indicator device of any of the preceding embodiments, wherein the first housing further comprises a second drain passage between the first major surface and the second major surface.

Embodiment 39

The microbial indicator device of any of the preceding embodiments, wherein the second drain passage is fluidically coupled with the second cavity and the first cavity.

Embodiment 40

The microbial indicator device of any of the preceding embodiments, wherein the second drain passage is fluidically coupled with the second cavity and the first filter cavity.

Embodiment 41

The microbial indicator device of any of the preceding embodiments, wherein the filter membrane has an average pore size of no greater than 0.4 microns.

Embodiment 41a

The microbial indicator device of any of the preceding embodiments, wherein the filter membrane has an average pore size of no greater than 0.2 microns.

Embodiment 42

The microbial indicator device of any of the preceding embodiments, wherein the filter membrane is a TIPS membrane.

Embodiment 43

The microbial indicator device of any of the preceding embodiments, wherein the filter membrane has a larger pore size on the first side relative to the second side.

Embodiment 44

The microbial indicator device of any of the preceding embodiments, wherein a portion of the second fluidic path is defined by a recessed portion on the first major surface of the first housing.

Embodiment 45

The microbial indicator device of any of the preceding embodiments, wherein a majority of the second fluidic path is defined by a recessed portion on the first major surface of the first housing.

Embodiment 46

The microbial indicator device of any of the preceding embodiments, wherein all of the second fluidic path is defined by a recessed portion on the first major surface of the first housing.

Embodiment 47

The microbial indicator device of any of the preceding embodiments, wherein a portion of the first cavity is defined by a recessed portion on the first major surface of the first housing.

Embodiment 48

The microbial indicator device of any of the preceding embodiments, wherein a portion of the funneling cavity is defined by a recessed portion on the first major surface of the first housing.

Embodiment 49

The microbial indicator device of any of the preceding embodiments, wherein a portion of the vent is defined by a recessed portion on the first major surface of the first housing.

Embodiment 50

The microbial indicator device of any of the preceding embodiments, further comprising a laminating film adjacent the first major surface of the first housing.

Embodiment 51

The microbial indicator device of any of the preceding embodiments, further comprising a one-way valve coupled to the first coupling portion and configured to prevent backflow through the first coupling portion.

Embodiment 52

The microbial indicator device of any of the preceding embodiments, wherein the first cavity is positioned such that the liquid flows from the first cavity to the second cavity using gravity when the container is in the second state.

Embodiment 52a

The microbial indicator device of any of the preceding embodiments, wherein the first housing is positioned such that a side portion is parallel to a longitudinal axis.

Embodiment 53

The microbial indicator device of any of the preceding embodiments, further comprising a carrier, wherein the source of biological activity is disposed thereon.

Embodiment 53a

The microbial indicator device of any of the preceding embodiments, wherein the source of biological activity is either killed by a successful disinfection cycle, or survives if the disinfection cycle is not adequate.

Embodiment 54

The microbial indicator device of any of the preceding embodiments, wherein the carrier is a nonwoven polymer.

Embodiment 55

The microbial indicator device of any of the preceding embodiments, wherein the carrier comprises a nutrient medium.

Embodiment 56

The microbial indicator device of any of the preceding embodiments, wherein the source of biological activity is a bacterial spore.

Embodiment 57

The microbial indicator device of any of the preceding embodiments, wherein the source of biological activity is ATP.

Embodiment 58

The microbial indicator device of any of the preceding embodiments, wherein the source of biological activity is a fungi.

Embodiment 59

The microbial indicator device of any of the preceding embodiments, wherein the source of biological activity is *Aspergillus niger*.

Embodiment 60

The microbial indicator device of any of the preceding embodiments, wherein the liquid comprises water.

Embodiment 60a

The microbial indicator device of any of the preceding embodiments, wherein the liquid is configured to activate a biological activity of the source of biological activity.

Embodiment 60b

The microbial indicator device of any of the preceding embodiments, further comprising a dry nutrient powder.

Embodiment 60c

The microbial indicator device of any of the preceding embodiments, wherein the dry nutrient powder is in a dissolvable container.

Embodiment 60d

The microbial indicator device of any of the preceding embodiments, wherein the dissolvable container is configured to partially dissolved based on a disinfection cycle in a reprocessing system.

Embodiment 60e

The microbial indicator device of any of the preceding embodiments, wherein the liquid is water that can be combined with the dry nutrient powder to form a nutrient medium.

Embodiment 61

The microbial indicator device of any of the preceding embodiments, wherein the liquid is a nutrient medium.

Embodiment 61a

The microbial indicator device of any of the preceding embodiments, wherein a cavity is formed from an indented portion of a housing.

Embodiment 61b

The microbial indicator device of any of the preceding embodiments, wherein the first cavity or the second cavity is formed from an indented portion of the first housing.

Embodiment 61c

The microbial indicator device of any of the preceding embodiments, wherein the first fluidic path or second fluidic path is partially established by indented portions formed from the first housing.

Embodiment 62

A kit, comprising:
the first housing of any of the preceding embodiments.

Embodiment 63

The kit of any of the preceding embodiments, further comprising:
the second housing of any of the preceding embodiments.

Embodiment 64

The kit of any of the preceding embodiments, further comprising:
the filter membrane of any of the preceding embodiments.

Embodiment 65

The kit of any of the preceding embodiments, further comprising:
one or more sealing elements.

Embodiment 66

The kit of any of the preceding embodiments, further comprising:
the container of any of the preceding embodiments.

Embodiment 67

The kit of any of the preceding embodiments, further comprising:
a one-way valve.

Embodiment 68

The kit of any of the preceding embodiments, further comprising:
a source of biological activity.

Embodiment 69

The kit of any of the preceding embodiments, further comprising:
a chemical indicator.

Embodiment 70

The kit of any of the preceding embodiments, further comprising:
a harness adapter comprising:
  a first conduit tube configured to couple the first coupling portion of the microbial indicator device of any of the preceding embodiments and the liquid input from a disinfection device;
  a second conduit tube configured to couple the second coupling portion of the microbial indicator device of any of the preceding embodiments and the liquid output from a disinfection device; and
  an outer cover member for holding both of the other ends of the first and second conduit tubes such that the disinfection agent can enter into the microbial indicator device of any of the preceding embodiments;

wherein the first conduit tube has a shape that corresponds to a conduit of an endoscope.

Embodiment 71

A method of operating a microbial indicator device, comprising:
obtaining the microbial indicator device of any of the preceding embodiments;
connecting the liquid input to a disinfection device;
allowing a disinfectant to flow through the second fluidic path of microbial indicator device;
wherein at least a portion of the source of biological activity is retained within the first filter cavity.

Embodiment 72

The method of any of the preceding embodiments, wherein, when the disinfectant contacts the first coupling portion, the disinfectant has a first pressure and, at the second coupling portion, the disinfectant has a second pressure, wherein the second pressure is at least 90 percent of the first pressure.

Embodiment 73

The method of any of the preceding embodiments, further comprising:
allowing the liquid to flow into the second cavity;
determining whether the source of biological activity is biologically active.

Embodiment 74

The method of any of the preceding embodiments, further comprising:
fracturing the container, wherein the container is changed from the first state to the second state.

What is claimed is:

1. A microbial indicator device for liquid disinfection, comprising:
a first housing comprising:
a first cavity;
a source of biological activity, wherein the source of biological activity is fluidically coupled to the first cavity via a portion of a first fluidic path;
a first coupling portion having a first channel extending longitudinally therethrough that defines a portion of a second fluidic path, wherein the first coupling portion is fluidically coupled to the source of biologically activity via the second fluidic path;
a filter membrane positioned in the second fluidic path, wherein the filter membrane has a first side and a second side, wherein the second fluidic path is established between the first coupling portion and the second side, and
a vent, wherein the vent is fluidically coupled to a portion of the first fluidic path; and
wherein the filter membrane has effective porosity sufficient to retain at least a portion of the source of biological activity on the first side.

2. The microbial indicator device of claim 1, wherein the filter membrane has a filter membrane surface area and the first coupling portion has an inlet area partially defined by a cross-section of the first channel, wherein a ratio of the filter membrane surface area to the inlet area is at least 100:1.

3. The microbial indicator device of claim 1, further comprising:
a chemical indicator that indicates a presence of a disinfectant.

4. The microbial indicator device of claim 3, further comprising:
a third cavity positioned in the second fluidic path, wherein the third cavity is positioned in the first housing and configured to house the chemical indicator, wherein the third cavity is fluidically coupled to the first coupling portion via the second fluidic path.

5. The microbial indicator device of claim 1, further comprising a second housing.

6. The microbial indicator device of claim 5, wherein the second side of the filter membrane is fluidically coupled to a second coupling portion with a channel extending longitudinally therethrough and positioned within the second housing.

7. The microbial indicator device of claim 5, wherein the second housing comprises one or more side portions and the first housing comprises one or more side portions, wherein the one or more side portions of the first housing are configured to mate with the one or more side portions of the second housing.

8. The microbial indicator device of claim 5, wherein the filter membrane is sandwiched between the first housing and the second housing.

9. The microbial indicator device of claim 1, further comprising a second cavity positioned in the first housing and configured to house the source of biological activity, wherein the second cavity is fluidically coupled to the first cavity via the first fluidic path.

10. The microbial indicator device of claim 9, further comprising a container containing a liquid and being dimensioned to be positioned in the first cavity, at least a portion of the container being frangible, the container having a first state in which the container is intact and the liquid is not in fluid communication with an interior of the first cavity and a second state in which the container is fractured and the liquid is in fluid communication with the first cavity.

11. The microbial indicator device of claim 10, further comprising a funneling cavity positioned adjacent to the first cavity and positioned within a portion of the first fluidic path, wherein the funneling cavity is configured to direct the liquid when the container is in the second state towards the second cavity.

12. The microbial indicator device of claim 9, wherein the first housing further comprises a first major surface, a second major surface, and a first drain passage formed from the first housing extending between the first major surface and the second major surface, wherein the first drain passage is fluidically coupled with the second cavity and the first cavity.

13. The microbial indicator device of claim 1, wherein the filter membrane has an average pore size of no greater than 0.2 microns.

14. The microbial indicator device of claim 1, wherein a resistance to flow of the filter membrane is no greater than 55 mm$^{-3}$ at 25 degrees C.

15. A method of operating a microbial indicator device, comprising:
connecting a first coupling portion of the microbial indicator device comprising:
a first housing comprising:
a first cavity;

a source of biological activity, wherein the source of biological activity is fluidically coupled to the first cavity via a portion of a first fluidic path;

the first coupling portion having a first channel extending longitudinally therethrough that defines a portion of a second fluidic path, wherein the first coupling portion is fluidically coupled to the source of biologically activity via the second fluidic path;

a filter membrane positioned in the second fluidic path, wherein the filter membrane has a first side and a second side, wherein the second fluidic path is established between the first coupling portion and the second side, and a vent, wherein the vent is fluidically coupled to a portion of the first fluidic path; and wherein the filter membrane has effective porosity sufficient to retain at least a portion of the source of biological activity on the first side;

allowing a disinfectant to flow through the second fluidic path of the microbial indicator device;

wherein at least a portion of the source of biological activity is retained within a first filter cavity.

16. The method of claim 15, wherein the microbial indicator device comprises a second housing, wherein the second side of the filter membrane is fluidically coupled to a second coupling portion with a channel extending longitudinally therethrough and positioned within the second housing, wherein, when the disinfectant contacts the first coupling portion, the disinfectant has a first pressure and, at the second coupling portion, the disinfectant has a second pressure, wherein the second pressure is at least 90 percent of the first pressure.

17. The method of claim 15, wherein the microbial indicator device comprises a container containing a liquid and being dimensioned to be positioned in the first cavity, at least a portion of the container being frangible, the container having a first state in which the container is intact and the liquid is not in fluid communication with an interior of the first cavity and a second state in which the container is fractured and the liquid is in fluid communication with the first cavity;

the method further comprising:
fracturing the container, wherein the container is changed from the first state to the second state;
allowing the liquid to flow into a second cavity;
determining whether the source of biological activity is biologically active.

18. A microbial indicator device for liquid disinfection, comprising:
a first housing comprising:
a first cavity;
a source of biological activity, wherein the source of biological activity is fluidically coupled to the first cavity via a portion of a first fluidic path;
a first coupling portion having a first channel extending longitudinally therethrough that defines a portion of a second fluidic path, wherein the first coupling portion is fluidically coupled to the source of biologically activity via the second fluidic path;

a filter membrane positioned in the second fluidic path, wherein the filter membrane has a first side and a second side, wherein the second fluidic path is established between the first coupling portion and the second side, wherein the filter membrane has effective porosity sufficient to retain at least a portion of the source of biological activity on the first side; and wherein the filter membrane has a filter membrane surface area and the first coupling portion has an inlet area partially defined by a cross-section of the first channel, wherein a ratio of the filter membrane surface area to the inlet area is at least 100:1.

* * * * *